United States Patent
Leow et al.

(10) Patent No.: US 11,446,350 B2
(45) Date of Patent: Sep. 20, 2022

(54) COMPOSITION FOR DELAYING AGING PROCESS AND INCREASING LONGEVITY IN A SUBJECT AND METHODS THEREOF

(71) Applicant: MALAYSIAN PALM OIL BOARD, Selangor (MY)

(72) Inventors: Soon Sen Leow, Kajang (MY); Ravigadevi Sambanthamurthi, Kajang (MY); Kenneth C. Hayes, Kajang (MY)

(73) Assignee: MALAYSIAN PALM OIL BOARD, Selangor (MY)

( * ) Notice: Subject to any disclaimer, the term of this patent is extended or adjusted under 35 U.S.C. 154(b) by 0 days.

(21) Appl. No.: 16/979,154

(22) PCT Filed: Mar. 8, 2019

(86) PCT No.: PCT/MY2019/050017
§ 371 (c)(1),
(2) Date: Sep. 8, 2020

(87) PCT Pub. No.: WO2019/172747
PCT Pub. Date: Sep. 12, 2019

(65) Prior Publication Data
US 2020/0397844 A1 Dec. 24, 2020

(30) Foreign Application Priority Data
Mar. 8, 2018 (MY) .............................. 2018700929

(51) Int. Cl.
| | | |
|---|---|---|
| A61K 36/889 | (2006.01) |
| A23L 33/105 | (2016.01) |
| A61P 39/00 | (2006.01) |
| A61K 47/12 | (2006.01) |
| A61K 47/14 | (2017.01) |
| A61K 47/26 | (2006.01) |

(52) U.S. Cl.
CPC .......... *A61K 36/889* (2013.01); *A23L 33/105* (2016.08); *A61K 47/12* (2013.01); *A61K 47/14* (2013.01); *A61K 47/26* (2013.01); *A61P 39/00* (2018.01); *A23V 2002/00* (2013.01)

(58) Field of Classification Search
None
See application file for complete search history.

(56) References Cited

U.S. PATENT DOCUMENTS

2015/0258164 A1 9/2015 Murdock et al.
2016/0000854 A1* 1/2016 Osborne ................. A61P 19/10
424/722

FOREIGN PATENT DOCUMENTS

WO 2006-014979 A2 2/2006

OTHER PUBLICATIONS

Balasundram et al. (2005) Asia Pac. J. Clin. Nutr. 14(Suppl.) 575 (Year: 2005).*
Bolsinger et al. (2014) J. Nutr. Sci. vol. 3 e5 (11 pages). (Year: 2014).*
Osborne et al. (2014) J. Aids Clin. Res. 5:12 (5 pages). (Year: 2014).*
Sun et al., "Acai palm fruit (Euterpe oleracea mart.) pulp improves survival of flies on a high fat diet" Experimental Gerontology, 2010.
Peixoto et al., "An anthocyanin rich extract of acai (Euterpe precatoria Mart.) increases stress resistance and retards aging related markers in Caenorhabditis elegan" Journal of Agricultural and Food Chemistry, 2016.
Leow et al., "Drosophila larvae fed palm fruit juice (PFJ) delay pupation via expression regulation of hormetic stress response genes linked to aging and longevity." Experimental Gerontology, Mar. 15, 2018.

* cited by examiner

*Primary Examiner* — Russell G Fiebig
(74) *Attorney, Agent, or Firm* — Maschoff Brennan

(57) ABSTRACT

The present invention relates to processes and composition meant for delaying ageing process in a subject comprising of palm fruit juice whole or its fractions, alone or in combination with other components in the form of a composition. Palm Fruit Juice alone or in combination with other additives can be administered preferably orally in pharmaceutically acceptable dosage forms.

5 Claims, 2 Drawing Sheets

COMPOSITION FOR DELAYING AGING PROCESS AND INCREASING LONGEVITY IN A SUBJECT AND METHODS THEREOF

FIELD OF INVENTION

The present invention relates to composition and methods for delaying ageing process and increasing longevity in a subject, and more particularly to compositions comprising palm fruit juice whole or its fractions, alone or in combination with other components in increasing lifespan or delaying ageing process.

BACKGROUND OF INVENTION

Ageing is a time-associated progressive decline in biological functions. Ageing refers to the various processes of wear and tear that affect an organism continuously. Ageing is associated with prolonged or chronic inflammation. It is a complex process defined by a decreased capacity to tolerate or respond to various stresses, and an increased predisposition to various diseases. Ageing leads to reduced life quality and increased medical costs seen in the elderly. The nine hallmarks of ageing include altered intercellular communication, cellular senescence, deregulated nutrient sensing, epigenetic alterations, genomic instability, loss of proteostasis, mitochondrial dysfunction, stem cell exhaustion, as well as telomere attrition. Based on these hallmarks, three main paradigms or research orientations have been distinguished in biological research on ageing i.e., 'compressed morbidity', 'decelerated ageing' and 'arrested ageing'. Compressed morbidity refers to the most conventional of these research agendas. Its goal is to forestall all chronic ailments of old age by intervening in the underlying molecular processes. In this model, the ultimate goal is to seek increases in average human life expectancy, but not in maximum human lifespan. The realization of this paradigm should result in a society with many more old people who have active roles until their final, swiftly fatal, decline.

As a considerably more ambitious agenda, the decelerated ageing approach seeks to slow down the fundamental processes of ageing to the extent that average life expectancy and maximum lifespan are increased. Finally, the most radical of the three research approaches seeks to 'cure' ageing. The goal of arrested ageing is to continually restore vitality and bodily function by removing the damage that is inevitably caused by metabolic processes.

Many theories have been proposed to explain ageing, and they may be grouped into evolutionary, molecular, cellular and systemic theories. Evolutionary theories of ageing seek to explain its underlying causes. They predict that there are certain genes that provide selective advantages early in life with deleterious lifespan effects later in life, for example longevity insurance genes related to somatic maintenance versus reproduction.

Current evolutionary explanations of ageing and limited longevity of biological species are based on two major evolutionary theories: the mutation accumulation theory and the antagonistic pleiotropy theory. These two theories can be summarized as follows:

Mutation accumulation theory: From the evolutionary perspective, ageing is an inevitable result of the declining force of natural selection with age. For example, a mutant gene that kills young children will be strongly selected against (will not be passed to the next generation) while a lethal mutation with effects confined to people over the age of 80 will experience no selection because people with this mutation will have already passed it to their offspring by that age. Over successive generations, late-acting deleterious mutations will accumulate, leading to an increase in mortality rates late in life.

Antagonistic pleiotropy theory: Late-acting deleterious genes may even be favoured by selection and be actively accumulated in populations if they have any beneficial effects early in life. Note that these two theories of ageing are not mutually exclusive, and both evolutionary mechanisms may operate at the same time. The main difference between the two theories is that in the mutation accumulation theory, genes with negative effects at old age accumulate passively from one generation to the next while in the antagonistic pleiotropy theory, these genes are actively kept in the gene pool by selection In line with the evolutionary theories of ageing, two major correlations underlie the biology of ageing, i.e. the negative correlation between lifespan and reproduction, as well as the positive correlation between lifespan and stress tolerance. Moderate stress could have beneficial effects in stimulating the innate defence resources of the body, thus boosting its ability to cope with higher stress levels and slowing the ageing process, while prolonged or severe stress exposure exhausts the defence mechanisms, causing drastic accumulation of errors and physiological abnormalities, thus accelerating the ageing process. Also known as the hormesis effect, moderate stress stimulates the expression of genes responsible for preventing or eliminating genetic errors.

Phytochemicals provide longevity effects via evolutionarily conserved mechanisms involved in nutrient-, energy- and stress-sensing pathways, which include the insulin/insulin-like growth factor 1 signalling (IIS) pathway, the target of rapamycin (TOR) pathway, the sirtuin-governed protein deacetylation integrating IIS and TOR pathways, the p38 MAPK stress-responsive signalling pathways and the non-selective autophagy pathway for cellular, organellar and macromolecular degradations. The complex effects of exogenous antioxidants such as phytochemicals in model organisms confirm to the present view that free radicals contrary to being damaging agents, may also be involved in signalling pathways and mediate beneficial response reactions on the basis of adaptive hormetic mechanisms which involve mild and repeated stresses. In *Caenorhabditis elegans* for example, mutants with increased lifespan have stress-responsive abilities towards heat, ultraviolet radiation and reactive oxidants. Hormetic agents such as caloric restriction, resveratrol, rapamycin, metformin, p53-inducing agents, physical exercise, heat shock, hypoxia and certain medical interventions, are able to inhibit the TOR pathway and/or increase ageing tolerance to complications of age-related diseases by protecting organisms from stronger stresses.

Phytochemicals extensively known as anti-ageing compounds are quercetin, epicatechin, curcumin and resveratrol. The positive actions of phytochemicals on ageing can be a result of numerous underlying mechanisms, including their antioxidant protection from macromolecular damage, effects on multiple molecular pathways which regulate lifespan and stimulating stress resistance as a result of hormesis.

Emerging studies showed that some phytochemicals have potential in reducing risk of chronic diseases, although they are not considered essential nutrients. Most phytochemicals are secondary plant metabolites which are present in a large variety of foods including fruit, vegetables, cereals, nuts and cocoa/chocolate as well as in beverages including juice, tea, coffee and wine. More than 1 g of phytochemicals per day is commonly ingested with the diet.

There are seven main categories of phytochemicals, including phenolic compounds, terpenes, betalians, organosulfides, indoles/glucosinolates/sulfur compounds, protein inhibitors and other organic acids. Phenolic compounds, also known as polyphenols, are the largest, most studied group. For example, tea flavan-3-ols (epigallocatechin gallate, EGCG), berry anthocyanins, soy isoflavones, and grape stibenoids resveratrol are in this category. Provitamin A carotenes from carrots and pumpkins, limonene from oils of citrus and cherries, saponins from legumes belong to terpenes. Although tocopherol (vitamin E) and omega-3 fatty acids are included in terpenes as phytochemicals and may have anti-ageing properties. However, these compounds affect ageing via different mechanisms and do not provide a wholesome approach towards delaying ageing, and increasing longevity.

Oxidative stress is considered to be substantial, if not crucial, in the initiation and development of many conditions and diseases, including: inflammation, autoimmune diseases, cataract, cancer, Parkinson's disease, arteriosclerosis and ageing. Oxidative stress plays a role in heart diseases, neurodegenerative diseases, cancer and in the ageing process. An imbalance between antioxidants and free radical results in oxidative stress, will/may lead to cellular damage At present, most antioxidants are manufactured synthetically, belonging to the class of synthetic antioxidants. The main disadvantage of synthetic antioxidants is the side effects when consumed in vivo. Plants are potential sources of invaluable antioxidants. Natural or phytochemical antioxidants are secondary metabolites in plants such as phenolic acids, flavonoids and carotenoids, which are amongst the antioxidants produced by plants for their sustenance. Recently, phenolics and flavonoids have been considered as great antioxidants and proved to be more effective than Vitamin C, E and carotenoids. The antioxidant properties of phenolic and flavonoid compounds are mediated by the following mechanisms:
(1) scavenging radical species such as ROS/reactive nitrogen species (RNS);
(2) suppressing ROS/RNS formation by inhibiting some enzymes or chelating trace metals involved in free radical production;
(3) up regulating or protecting antioxidant defense The reduction activity of phenolic and flavonoid compounds depends on the number of free hydroxyl groups in the molecular structure, which would be strengthened by steric hindrance.

While there is no unified mechanism underlying the ageing process, a large body of evidence indicates that increased generation of ROS which are chemically reactive molecules with most of them containing oxygen and unpaired electrons is one of the major triggers of ageing. Indeed, there is a strong correlation between chronological age and the levels of ROS generation and oxidative damage of tissues. ROS are primarily produced by mitochondrion during energy production (about 2% of total oxygen consumption was funneled to ROS). Excess amount of ROS induces oxidation of fatty acids and proteins and causes oxidative damage of DNA that may lead to cellular senescence, functional alterations and pathological conditions. Moreover, several age-related chronic diseases such as cardiovascular diseases, diabetes and cancer are associated with severe increases in oxidative stress. Superoxide anion (O2-), the major form of ROS produced in mitochondrion, is quickly converted to hydrogen peroxide by two intracellular enzymes, SOD1 in cytosol and SOD2 in the matrix of mitochondria. Hydrogen peroxide is further deactivated to become water and oxygen by catalase or glutathione peroxidases (GPx). Endogenous antioxidant GSH and exogenous antioxidants including vitamins C and E are also important ROS scavengers. Cells maintain redox balance and thus its normal function through generation and destruction of ROS. However, this balance can be interrupted by environmental factors and ageing that leads to an excessive bioavailability of ROS. In fact, mitochondrial integrity declines as a function of age, and ROS is increased but, GPx is decreases during ageing. Given that ROS-induced oxidative stress plays a key role in driving the ageing process, reducing ROS is proposed as a leading strategy to delay ageing and related degenerative diseases. Some food-derived phytochemicals may play a significant role in maintaining the ROS-antioxidant balance. Phytochemicals can directly scavenge ROS.

Many phytochemicals are found to have antioxidant activity capable of scavenging ROS, a property that may be primarily attributable to their phenolic hydroxyl groups.

Accordingly, there is a need to develop compositions that are derived from reliable natural resources, and related methods of treatment for delaying ageing and increase lifespan of an organism, especially human beings, through variety of mechanisms.

SUMMARY OF THE INVENTION

The present embodiment relates to a composition for delaying ageing process in a subject or an organism, the composition included Palm Fruit Juice (PFJ) extracts, whole or its fractions, in substantial amount alone or in combination with other components.

In another aspect, a composition for regulating hormetic stress response genes linked to ageing and longevity, to delay ageing in a human subject is provided. The composition includes PFJ extracts in whole or its fractions, alone or in combination with suitable components. The organism may be a human subject.

In another aspect, a composition for down regulating tor-related regulatory network is provided. The composition includes administering to an organism a composition having PFJ extracts in whole or its fractions, alone or in combination with suitable components. The organism may be a human subject.

In an aspect, the composition includes bioactive water-soluble compounds derived from PFJ, wherein the water-soluble compounds primarily include phenolics, shikimic acid, and soluble fibre, and the phenolic compounds primarily include p-hydroxybenzoic acid and three caffeoyl shikimic acid isomers.

In another aspect, a composition that delays the ageing process and promote longevity via expression regulation of hormetic stress response gene linked to ageing and longevity, more specifically Tor, Sod2 and various heat shock proteins.

In another aspect, such that the extract is obtained from any part of oil palm fruit bunch or palm oil mill effluents (POME) such as vegetation liquor (aqueous stream) or the non-aqueous stream.

In an aspect, a method for increasing lifespan or longevity, or delaying ageing, in an organism is provided. The method includes administering to the organism a composition having PFJ extracts in whole or its fractions, alone or in combination with suitable components. The organism may be a human subject.

In another aspect, a method for regulating hormetic stress response genes linked to ageing and longevity, to delay ageing in a human subject. The method includes administering to the organism a composition having PFJ extracts in whole or its fractions, alone or in combination with suitable components. The organism may be a human subject.

In another aspect, a method of down regulating tor-related regulatory network is provided. The method includes administering to an organism a composition having PFJ extracts in whole or its fractions, alone or in combination with suitable components. The organism may be a human subject.

In an aspect, a use of a composition having PFJ extracts in whole or its fractions, alone or in combination with suitable components for increasing longevity and delaying ageing in an organism is provided. The organism may be a human subject.

DETAILED DESCRIPTION OF PREFERRED EMBODIMENT

Figure 1:
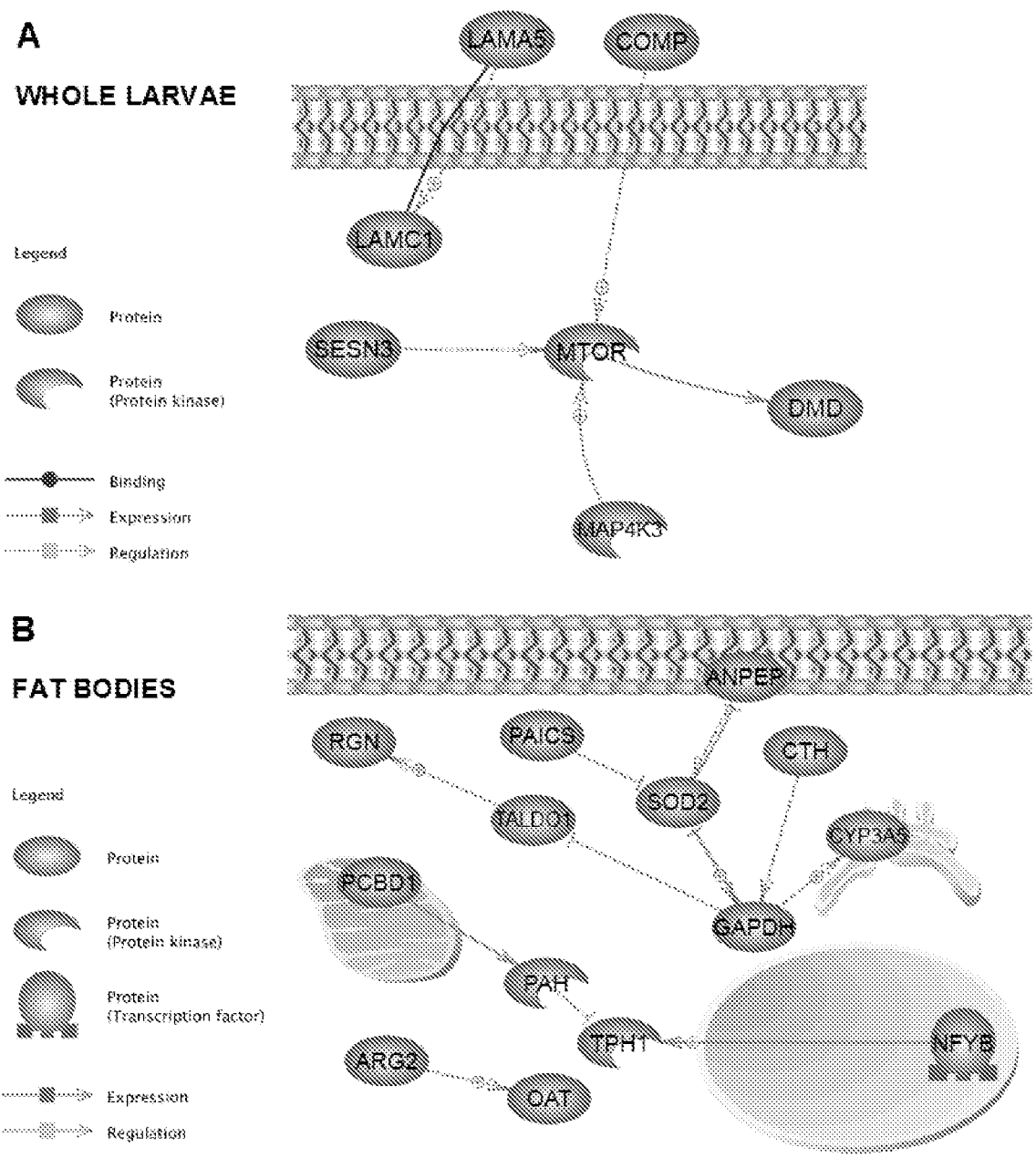
FIG. 1A-1B illustrate Pathway Studio regulatory network analysis results for Network of genes down-regulated by PFJ in whole fruit fly larvae; and for Network of genes up-regulated by PFJ in larval fat bodies, respectively.
Figure 2:
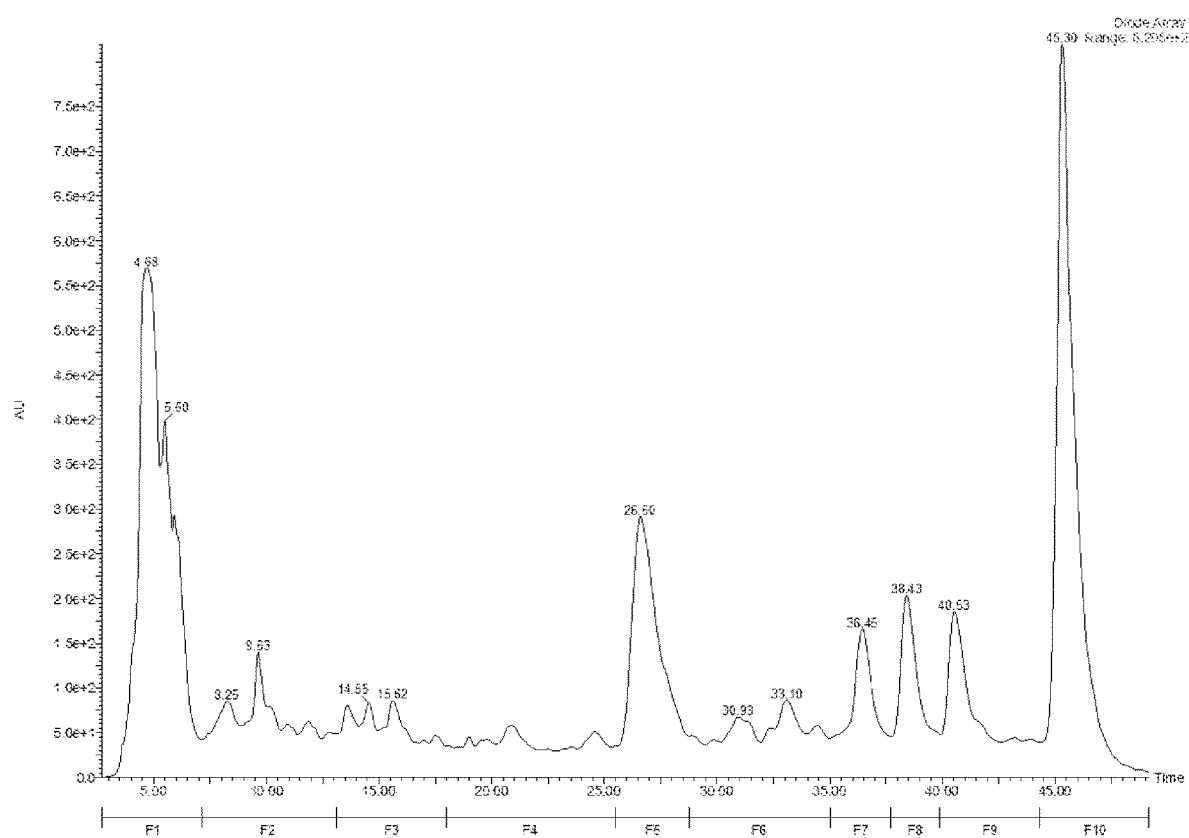
FIG. 2 illustrates a preparative liquid chromatogram of PFJ fractions viewed at 280 nm ultraviolet wavelength with the major components for fractions F1, F5 and F7 being shikimic acid and soluble fibre, p-hydroxybenzoic acid and caffeoylshikimic acid respectively.

Definitions and Abbreviations: For the purposes of present invention following terms and abbreviation are to be read in accordance with the definitions and expanded forms so provided.
ANOVA: analysis of variance;
CAFÉ: capillary feeding;
cDNA: complementary deoxyribonucleic acid;
cRNA: complementary ribonucleic acid;
Ct: threshold cycle;
dFOXO: *Drosophila* forkhead transcription factor;
dILPs: *Drosophila* insulin-like peptides;
GAE: gallic acid equivalent;
IIS: insulin/insulin-like growth factor 1 signaling;
mRNA: messenger ribonucleic acid;
PFJ: palm fruit juice;
PI3K: phosphatidylinositol-3-kinase;
PLSD: partial least squares discriminant;
qRT-PCR: quantitative reverse transcription-polymerase chain reaction;
SBD: Standard Brandeis Diet;
SD: standard deviation;
SEM: standard error of the mean;
SO: superoxide dismutase;
TOR: target of rapamycin The term "pharmaceutically acceptable carrier" is defined as any safe material that acts as a vehicle for delivery including but not limited to: water, saline, starches, sugars, gels, lipids, waxes, paraffin derivatives, glycerols, solvents, oils, proteins, talc, glycols, electrolyte solutions, alcohols, gums, fillers, binders, cellulose, magnesium stearate, emulsifiers, humectants, preservatives, buffers, colorants, emollients, foaming agents, sweeteners, thickeners, surfactants, additives, solvents, lubricants or the like. The pharmaceutically acceptable carrier includes one or more compatible solid or liquid filler diluents or encapsulating substances that are suitable for administration to humans or animals.

The term "therapeutically effective amount" is defined as an amount of one or more of the active ingredients that comprise this invention, administered to an animal or human at a dose such that efficacy of the treatment can bring about delay in ageing or related and underlying processes and pathways. The formulation may be presented in unit dosage form and may be prepared by any method well known in the art of pharmacy. The active ingredients of the formulation may be presented in liquid or solid, in ampoules or vials (preferably amber) or pill form and can be further incorporated with a pharmaceutically acceptable carrier, appropriate for the method of delivery as deemed appropriate by one skilled in the art.

The oil palm (*Elaeis guineensis* and *Elaeis oleifera*) fruit bunch contains bioactive water-soluble compounds. The water-soluble compounds are rich in phenolics, shikimic acid, and soluble fibre extracted from the aqueous vegetation liquor produced from oil palm milling as palm fruit juice (PFJ). The phenolic compounds include p-hydroxybenzoic acid and three caffeoylshikimic acid isomers.

The composition known as palm fruit juice (PFJ) containing oil palm phenolics is obtained from oil palm fruit bunch or as a by-product from oil palm (*Elaeis guineensis* and *E. oleifera*) fruit milling. It contains among others, shikimic acid, soluble fibre and various phenolic acids including p-hydroxybenzoic acid and three caffeoylshikimic acid isomers. PFJ has also been described interchangeably as water-soluble bioactives and OPP (oil palm phenolic extract). PFJ also has demonstrated beneficial health properties in various biological models. This disclosure describes the effects of supplementing increasing concentrations of PFJ and different PFJ fractions in modulating growth dynamics as well as promoting anti-ageing and longevity.

In an embodiment, a method delaying the effects of ageing in a subject or organism are provided. The method includes administering palm fruit juice or a fraction thereof to a mammal in sufficient amount or frequency to delay the effects of ageing in the subject. In a preferred embodiment, the subject is a mammal or an insect. In another preferred embodiment, the subject is a human being. In yet another preferred embodiment, the human is Wherein the human is at least 5, 10, 20, 30, 40, 50, 60 or more years old. In yet another embodiment, the human is in utero.

In an embodiment, PFJ may be administered alone or in combination with other additives in the form of a composition for inducing delay in ageing process in a subject.

The composition further includes bioactive lipid- and water-soluble compounds of POME or Oil Palm milling processes, wherein the water-soluble compounds primarily include phenolics, shikimic acid, and soluble fibre and the phenolic compounds primarily comprising p-hydroxybenzoic acid and three caffeoylshikimic acid isomers.

In another preferred embodiment, PFJ alone or in combination with other additives can be administered preferably orally in pharmaceutically acceptable dosage forms for ageing delaying effects. In yet another aspect the composition comprises of a pharmaceutically acceptable carrier, preservative agent, sweetener, flavoring agent, coloring agent, and a combination thereof. In yet another embodiment, aspect the composition comprises of an aqueous carrier.

In yet another embodiment, the aqueous carrier is selected from the group consisting of spring water, filtered water, distilled water, carbonated water, juices, and a combination thereof.

In yet another aspect wherein the pharmaceutically acceptable carrier may be stabilizers, carriers, extenders, and other suitable substances.

In yet another aspect pharmaceutically acceptable carrier further comprises one or more selected from the group consisting of water, saline, starches, sugars, gels, lipids, waxes, glycerol, solvents, oils, liquids, proteins, glycols, electrolyte solutions, alcohols, fillers, binders, emulsifiers, humectants, preservatives, buffers, colorants, emollients, foaming agents, sweeteners, thickeners, surfactants, additives and solvents and mixtures thereof.

In yet another aspect pharmaceutically acceptable carrier is made suitable for oral, injectable or external administration and further comprises the form of a solid, liquid, powder, paste, gel, tablet, granule, foam, pack, aerosol, solvent, diluent, capsule, pill, drink, liposome, syrup, solution, suppository, emulsion, enema, suspension, dispersion, food, bio-delivery agents and mixtures thereof.

The form of a pharmaceutically acceptable carrier used to deliver the treatment to a human or animal is all inclusive not limited to a cream, solid, liquid, powder, paste, gel, tablet, granule, foam, pack, ointment, aerosol, solvent, tablet, diluent, capsule, pill, drink, liposome, syrup, solution, suppository, emulsion, suspension, dispersion, food, bolus, electuary, paste or other bio-delivery system or agent.

The compositions of the present embodiments include pharmaceutically acceptable carriers and delivery systems adapted for varying route of administration such as topical, enteral and parenteral including but not limited to: oral, rectal, nasal, vaginal, subcutaneous, intramuscular, intravenous, intratumor, intraperitoneal, intramammary, intraosseous infusion, transmucosal, transdermal, epicutaneous, intracutaneous, epidural, intrathecal, inhalation, opthalamic or other suitable route.

The compositions for administration include aqueous and non-aqueous isotonic sterile solutions, which may contain anti-oxidants, oils, glycols, alcohols, buffers, bacteriostats, solutes, suspending agents, biodegradable time-release polymers, surfactants, preservatives and thickening agents.

The compositions of the present invention adapted for oral administration may contain a predetermined quantity of the active ingredient i.e. palm fruit juice or its fractions and take the form of sprays, liquids, syrups, beverages, capsules, powders, granules, solutions, suspensions, tablets, food, lozenges or any other form in which the active ingredients are taken by mouth and absorbed through the alimentary canal.

The compositions may also incorporate the active ingredients with pharmaceutically acceptable carriers such as buffers, gums, surfactants, fillers, preservatives, bulking agents, colorants, diluents, flavoring agents, emulsifiers, sugars, oils, cellulose, gelatin, flour, maltodextrose, time release polymers and the like.

In another embodiment, the composition may be incorporated into a tablet (including capsule, caplet, and the like). Suitable bases are known to those skilled in the art to include fillers, binders, coatings, excipients and combinations thereof. For example, base ingredients include, but are not limited to, plant cellulose, natural silica, magnesium stearate, wax, vegetable glycerides, vegetable stearate, and a combination thereof.

In an embodiment, a method for production of a pharmaceutical form which includes mixing an active component and pharmaceutically acceptable carrier with suitable adjuvants wherein said active component comprises an effective amount of a composition including palm fruit juice or its fractions.

In yet another embodiment, the solid, soft or liquid substances are used as the pharmaceutically acceptable carrier.

In an embodiment, a method for inducing expression of a heat shock protein, superoxide dismutase, and/or a Tor protein in a subject in need thereof is provided. The method includes administering palm fruit juice or a fraction thereof to a subject in sufficient amount or frequency to induce the expression of the heat shock protein, superoxide dismutase, and/or a Tor protein in the mammal.

In a preferred embodiment, a method for regulating hormetic stress response genes linked to ageing and longevity, to delay ageing in a human subject. The method includes administering to the organism a composition having PFJ extracts in whole or its fractions, alone or in combination with suitable components. The organism may be a human subject.

In another preferred embodiment, a method of down regulating tor-related regulatory network is provided. The method includes administering to an organism a composition having PFJ extracts in whole or its fractions, alone or in combination with suitable components. The organism may be a human subject.

In the current disclosure, *Drosophila melanogaster*, at any stage of their development, is used a preferred biological model to establish evidence related to the growth and development altering effects to enhance lifespan. It is common to administer experimental pro-longevity compounds over the entire adult lifespan of a test organism.

The fruit fly, *Drosophila melanogaster*, has been used for more than a century as a highly tractable genetic model for understanding human physiology and the molecular mechanisms of human diseases. The parallels between the genomes of *Drosophila* and humans and strong evolutionary conservation of key genes and pathways are key to leveraging this fruit fly to study human development, metabolism, and genetic diseases. Close to 75% of human disease-causing genes are believed to have a functional homologue in *Drosophila melanogaster*. The relatively short lifespan, short life cycle and large number of offspring are beneficial for genetic research as new fly lines can be quickly and easily created at comparatively low cost. The relatively short lifespan allows for complex questions on physiological and developmental functions to be answered more quickly than in other model organisms, such as the mouse. In short, *Drosophila melanogaster* is a superior model organism for decoding the genetic mechanisms that affect clinically relevant complex human traits.

Experiments were conducted on *Drosophila* in particular in developmental stages and software were used to draw ontologies to human mechanisms were drawn through available software. Beneficial effects were observed when the PFJ was administered in the larval (developmental) or young adult (health span) stages. As such, experiments designed to identify pro-longevity compositions should be designed not only for studying their effects at the adult stage but also at the developmental (e.g. larval/foetal) stage to amplify this potential and take this stage specificity into account. Also, early-life nourishment exerts long-term influences upon adult physiology, disease risk, and lifespan.

Microarray gene expression analysis on whole fruit fly larvae supplemented with PFJ revealed that development and morphogenesis processes were down-regulated compared to controls, with the down-regulation of a regulatory network involving the MTOR or Tor gene being most prominent. It is also important to emphasise that the regulatory networks plotted by the Pathway Studio software (Elsevier B.V., Amsterdam, Netherlands) in the current study were analysed using human gene orthologues of fruit fly genes identified as significantly regulated. Therefore, the results obtained from the regulatory network analysis could be further extrapolated and are likely relevant to humans.

The TOR signalling pathway is an attractive candidate for study with respect to ageing, as it has the potential to affect various processes having a major impact on growth. TOR belongs to a conserved group of serine/threonine kinases from the phosphatidylinositol kinase-related kinase family, and it plays a key role in connecting nutrients to anabolic processes and growth. Nutrients in general activate the nutrient-sensing TOR pathway, while their restriction or lack deactivates it. The TOR pathway is a key regulator of lifespan and health span in various species, whereas an overactive TOR pathway has been linked to various chronic diseases such as cancer, type 2 diabetes, age-related macular degeneration, obesity, atherosclerosis and neurodegeneration, all of which limit lifespan. Down-regulation of the TOR pathway by PFJ compositions extends lifespan in *Drosophila melanogaster*. TOR stimulates translation, inhibits autophagy, drives cellular hyperfunction as well as causes signalling resistance, and decreased TOR signalling correlates with oxidative stress resistance. As reviewed, at least four consistent effects were observed due to reduced TOR signalling, i.e. up-regulated mitochondrial oxidative phosphorylation, autophagy initiation, increased resistance to oxidative stress and improved cell protective metabolic response.

Functional enrichment analysis on gene ontologies (biological processes) showed that genes involved in defence response and determination of adult lifespan were up-regulated, while cell cycle and growth genes were down-regulated. Further, functional enrichment analysis of differentially expressed genes on gene ontologies (biological processes) using the GO-Elite software showed that transport and metabolic processes were up-regulated, while development and morphogenesis processes were down-regulated.

Regulatory network analysis using the Pathway Studio software (Elsevier B.V., Amsterdam, Netherlands) revealed that for the whole fruit fly larvae data, 35 out of the 127 up-regulated genes could be mapped onto human orthologues, but no relationships between these mapped genes could be identified. On the other hand, 22 out of 67 down-regulated genes could be mapped onto human orthologues, and 6 relationships were identified between the mapped genes, with 15 unconnected entities removed (FIG. 1A). Among the genes plotted in the regulatory network, the MTOR (mechanistic target of rapamycin) or Tor (target of rapamycin) gene appeared most important. The ImpE1 (ecdysone-inducible gene E1) gene was also found significantly down-regulated in whole fruit fly larvae supplemented with PFJ.

Using a similar cut off, microarray gene expression analysis on larval fat bodies showed that 161 genes were up-regulated, while 84 genes were down-regulated following PFJ supplementation, including various heat shock proteins For the larval fat bodies data, regulatory network analysis showed that 53 out of 161 up-regulated genes could be mapped onto human orthologues, and 13 relationships were identified between the mapped genes, with 27 unconnected entities removed (FIG. 1B). The SOD (superoxide dismutase) or Sod2 (superoxide dismutase 2) gene is one of the nodes plotted in this regulatory network.

Functional analysis revealed transport and metabolic processes were up-regulated, while development and morphogenesis processes, including the nutrient-sensing Tor gene, were down-regulated by PFJ, whereas microarray analysis of larval fat bodies found 161 genes were up-regulated, while 84 genes were down-regulated. Genes involved in defence response and determination of adult lifespan, including those encoding various heat shock proteins and the antioxidant enzyme Sod2, were up-regulated, while cell cycle and growth genes were down-regulated.

Thus, PFJ supplementation lengthened the growth stages in fruit fly larvae that was reflected in extended ageing of adult flies, suggesting that larval expression of hormetic stress response genes was linked to subsequent ageing and longevity. In an aspect, the PFJ supplementation delays ageing process via expression regulation of hormetic stress response genes linked to ageing and longevity, specifically Tor, various heat shock proteins, and Sod2

Based on the list of genes found significantly regulated in the larval fat bodies, it was found that various heat shock proteins were up-regulated following PFJ supplementation. Many of these heat shock proteins are related to pro-longevity in *Drosophila*. Heat shock proteins are defined by their ability to bind to denatured proteins and alter the folded structure of other proteins, as well as by the induction of their expression in response to stresses that cause protein denaturation, such as heat and oxidative stress. There are several possible mechanisms by which heat shock proteins may act to increase lifespan. By mediating either protein refolding or degradation, heat shock proteins counteract proteotoxicity and favour stress resistance. Further, Pathway Studio analysis also showed that a regulatory network related to SOD or Sod2 was up-regulated in the larval fat bodies following PFJ supplementation.

Transcriptomic analysis on whole fruit fly larvae and larval fat bodies revealed that PFJ supplementation generally lengthened the active stage of the fruit fly larvae and this may hence delay their ageing process via expression regulation of hormetic stress response genes linked to ageing and longevity, specifically Tor, various heat shock proteins, and Sod2. Further on mapping the up and down regulated gene with human orhtologoues MTOR or TOR pathway was identified significantly and therefore PFJ can be an important neutraceutical for delaying ageing in a subject.

EXAMPLES

Example 1: Preparation of PFJ and its Fractions

Liquid PFJ was obtained from aqueous oil palm milling vegetation liquor in two batches from Labu, Negeri Sembilan, Malaysia. The phenolic content of these stock solutions was determined using the Folin-Ciocalteu reagent.

PFJ fractions were extracted from liquid PFJ samples using ethyl acetate. The supernatant was evaporated (water bath temperature 55° C., rotation speed 35 rpm and pressure 5.5 kPa) by using a BUCHI R-205 rotary evaporator (BUCHI Labortechnik AG, Switzerland) and injected into a Waters Preparative AutoPurification High Performance Liquid Chromatography (HPLC) System, which includes a 2767 Sample Manager, a 2545 Binary Gradient Module, a System Fluidics Organiser, a 2489 UV/Vis Detector and the MassLynx Software with the FractionLynx Application Manager (Waters Corp., Milford, Mass.) for fraction separation.

Preparative HPLC separation was achieved using a reverse phase Waters Atlantis C18 5 μm column (Waters Corp., Milford, Mass.). A binary gradient system was used as the mobile phase, with phase A comprising distilled water containing 0.02% (v/v) trifluoroacetic acid and phase B comprising 70%:30% (v/v) methanol-acetonitrile. A flow rate of 20 mL/min and a pressure limit of $2.76 \times 10^4$ kPa were used. The gradient elution with a total run time of 55 min was as follows: started from 100% (v/v) phase A and 0% (v/v) phase B, increased to 32.5% (v/v) phase B over 40 min, then increased to 62.5% (v/v) phase B over 6 min and finally decreased to 0% (v/v) phase B over 9 min. Fractions as characterised by ultraviolet/visible (UV/VIS) detection at 280 nm UV wavelength were collected based on their retention time.

The fractions were then rotary evaporated and dried with a freeze dryer (Ilshin, South Korea) (temperature −55° C. and pressure 689.48 kPa) and kept at −80° C. until use. The phenolic content of these fractions was also determined using the Folin-Ciocalteu reagent.

Example 2: Preparation of Fruit Fly Diet

The fruit fly control Standard Brandeis Diet (SBD) used in the present study was prepared fresh prior to each experiment according to its composition.

Example 3: Fruit Fly Strain and Husbandry

Fruit flies (*Drosophila melanogaster*) genotype $w^{1118}$ were utilised for all experiments. Fruit fly feeding was conducted in five different experiments. The flies were housed in plugged and capped culture vials (Fisher Scientific, Waltham, Mass.) partially filled with 10 mL of the required diet. All stocks were maintained in incubators at 25° C. and a 12 h/12 h light/dark cycle. Humidity was maintained via water pans in the incubators at 70% humidity.

Example 4: PFJ Fraction-Related Experiment for Estimating Fruit Fly Adult Lifespan This example compared the control diet (SBD) (0 μg GAE/kcal) against 4 mL of PFJ (930 μg GAE/kcal diet) incorporated into that same diet, using a stock solution of PFJ (19,000 mg GAE/L). In addition, three other diets supplied major fractions of PFJ as dried powder having different GAE contents, i.e. 284 mg F1/kg diet (providing shikimic acid and soluble fibre with only trace μg GAE/kcal diet); 284 mg F5/kg diet (providing p-hydroxybenzoic acid and 654 μg GAE/kcal diet), and 284 mg F7/kg diet (providing caffeoylshikimic acid and 1055 μg GAE/kcal diet).

Survival study. To assess survival of adult flies related to PFJ intake, eclosed male fruit flies were allowed to age on

TABLE 1

| Composition of fruit fly diets | | | | | |
|---|---|---|---|---|---|
| Diet | Control (SBD) | x mL PFJ | PFJ F1 | PFJ F5 | PFJ F7 |
| Carbohydrate:fat:protein (% energy) | 83:05:12 | 83:05:12 | 83:05:12 | 83:05:12 | 83:05:12 |
| kcal/mL | 0.700 | 0.700 | 0.700 | 0.700 | 0.700 |
| Ingredients: | | | | | |
| Water (mL) | 100.000 | 100 − x | 100.000 | 100.000 | 100.000 |
| Methyl-4-hydroxybenzoate (g) | 0.280 | 0.280 | 0.280 | 0.280 | 0.280 |
| Agar (g) | 1.000 | 1.000 | 1.000 | 1.000 | 1.000 |
| Sucrose (g) | 10.500 | 10.500 | 10.500 | 10.500 | 10.500 |
| Flaked yeast (g) | 3.300 | 3.300 | 3.300 | 3.300 | 3.300 |
| Cornmeal (g) | 7.600 | 7.600 | 7.600 | 7.600 | 7.600 |
| $Na^+K^+$ tartrate (g) | 0.800 | 0.800 | 0.800 | 0.800 | 0.800 |
| $CaCl_2$ (g) | 0.100 | 0.100 | 0.100 | 0.100 | 0.100 |
| PFJ (mL), x = 2, 3, 4, 6, 8, 12 | 0.000 | x | 0.000 | 0.000 | 0.000 |
| PFJ-F1 (g), shikimic acid and soluble fibre | 0.000 | 0.000 | 0.284 | 0.000 | 0.000 |
| PFJ-F5 (g), p-hydroxybenzoic acid | 0.000 | 0.000 | 0.000 | 0.284 | 0.000 |
| PFJ-F7 (g), caffeoylshikimic acid | 0.000 | 0.000 | 0.000 | 0.000 | 0.284 |

All diets were made to 125 mL final volume (or 125 g weight) and were allowed to begin gelling before being added into fly holding vials.

For diet mixing, water was first brought to a boil and agar was mixed in slowly. Calcium chloride and methyl-4-hydroxybenzoate were then stirred into the solution along with the different amounts of PFJ or fractions tested. Finally, all the dry ingredients, including dextrose, cornmeal, flaked yeast and $Na^+K^+$tartrate) were blended into the mixture. As the mixture thickened, 10 mL of diet was pipetted into 40 mL plastic vials and set to cool under a towel to minimise exposure to dust. The 40 mL vials were stoppered with cotton overnight and finally refrigerated until use within a week.

the control diet (SBD) (without PFJ or its fractions and without yeast flakes sprinkled on top) for 90 days for analysis of adult lifespan assessed every ten days for comparison of the larval diets on survival. This provided an estimate of how the impact of PFJ and its fractions during larval development ultimately affected the survival rate of the eclosed fruit flies fed the control diet (SBD) until death, specifically testing the hypothesis that slowed larval growth and development observed in Experiments 1 and 2 would favour lifespan extension.

Example 5: Gene Expression Studies

The control group of larvae (n=20) was exposed to the control diet (SBD) alone, while the treatment group larvae (n=20) was exposed to that same diet with PFJ added (4 mL PFJ from 19,000 mg GAE/L stock solution providing 930 µg GAE/kcal diet) for five days of larval growth from the egg stage. Upon completion of the feeding regimen, whole fruit fly larvae (n=10) or extracted larval fat bodies (n=10) from each diet group were snap-frozen in liquid nitrogen and stored at −80° C. until the total RNA was extracted for gene expression analysis. Both whole fruit fly larvae and larval fat bodies were assessed because the fat body is an important organ in Drosophila nutrition and lifespan determination, and it was important to identify whether specific gene expression changes in this organ could be differentiated from those observed with the whole larvae in general.

Microarray Gene Expression Analysis

Total RNA was extracted from frozen whole fruit fly larvae (n=3 per control and test diet containing three to four larvae each) and larval fat bodies (n=2 per diet containing five fat bodies each) via the silica-membrane extraction column method by using the RNeasy Mini Kit (Qiagen, Inc., Valencia, Calif.). This was preceded by grinding in liquid nitrogen using mortar and pestle. Yield and purity of the total RNA samples obtained were assessed using the NanoDrop 1000A Spectrophotometer (Thermo Fisher Scientific, Waltham, Mass.). Integrity of the total RNA samples was assessed using the Agilent 2100 Bioanalyzer (Agilent Technologies, Santa Clara, Calif.) and Agilent RNA 6000 Nano Chip Assay Kit (Agilent Technologies, Santa Clara, Calif.).

Total RNA samples which were of high yield, purity and integrity were amplified using the GeneChip WT PLUS Reagent Kit (Affymetrix, Santa Clara, Calif.) from 100 ng of total RNA according to manufacturer's instructions. Following fragmentation and labelling, 3.5 µg of single-stranded cDNA was hybridised for 16 hours at 45° C. on Drosophila Gene 1.0 ST Array (Affymetrix, Santa Clara, Calif.) in the GeneChip Hybridization Oven 640 (Affymetrix, Santa Clara, Calif.). The GeneChips were then washed and stained in the Affymetrix GeneChip Fluidics Station 450 (Affymetrix, Santa Clara, Calif.) according to the manufacturer's instructions. Following this, the GeneChips were scanned using the Affymetrix GeneChip Scanner 3000 (Affymetrix, Santa Clara, Calif.). The raw gene expression data obtained are available at Gene Expression Omnibus (Edgar et al., 2002) (Accession number: GSE93222).

Data normalisation, quality control of the hybridisation and principal component analysis were performed with the Affymetrix Expression Console 1.4.0.38 software (Affymetrix, Santa Clara, Calif.), by using the default gene level RMA-Sketch processing algorithm. To identify differentially expressed genes, the Affymetrix Transcriptome Analysis Console 2.0.0.9 software (Affymetrix, Santa Clara, Calif.) was used. Gene level differential expression analysis was performed according to the default algorithm of the software, with genes having one-way unpaired between subject ANOVA p values <0.05 and fold changes >|1.30| considered differentially expressed. As only two groups i.e. control and treatment were compared, the one-way unpaired between subject ANOVA statistical analysis carried out was essentially a simple t-test. Two-way (gene and sample) hierarchical clustering of the significant genes was then carried out to ensure that the replicates of each condition were clustered to each other.

Functional enrichment analysis to assess changes in gene ontologies (biological processes) was then performed using the GO-Elite software (Zambon et al., 2012). The GO-Elite software ranks gene ontologies based on the hypergeometric distribution. Gene ontologies considered significantly changed had permuted p values <0.05, numbers of genes changed ≥2 and Z scores >2. Genes up- and down-regulated were analysed separately for each set of microarray data from whole fruit fly larvae and larval fat bodies in this functional enrichment analysis.

In addition, changes in regulatory networks were analysed using the Pathway Studio software (Elsevier B.V., Amsterdam, Netherlands). A network graphically represents the molecular relationships between genes or gene products, which are represented as nodes, while the biological relationships between the nodes are represented as edges. Nodes are displayed using various shapes that represent the functional class of the gene product, while edges are displayed with various patterned lines that describe the nature of the relationship between the nodes. Fruit fly (Drosophila melanogaster) genes were first mapped onto human (Homo sapiens) orthologues using Entrez gene identifiers. The Network Builder Advanced Direct Interactions Tool was then used to plot out regulatory networks of mapped genes. Genes up- and down-regulated were analysed separately for each set of microarray data from whole fruit fly larvae and larval fat bodies in this network analysis. After removing unconnected entities, the Localisation by Plain Membrane Layout was selected to display the regulatory networks in their related organelles.

Example 6: Real-Time qRT-PCR Validation

Two-step real-time quantitative reverse transcription-polymerase chain reaction (qRT-PCR) was conducted by using the custom $RT^2$ Profiler™ PCR Arrays (Qiagen, Inc., Valencia, Calif.) (Catalogue ID: CLAD22265), which are SYBR Green-optimised primer assays, to validate the obtained microarray data. This was performed on 40 differentially expressed target genes of interest and 5 reference genes (Table 2), which were selected based on the microarray data analysis carried out. The same aliquots of total RNA samples utilised in the microarray experiments were used for this real-time qRT-PCR validation. The $RT^2$ SYBR Green qPCR Mastermix (Qiagen, Inc., Valencia, Calif.) was also used for the assays.

Briefly, first-strand cDNA was generated from total RNA via reverse transcription using the $RT^2$ First Strand Kit (Qiagen, Inc., Valencia, Calif.). The first-strand cDNA generated was used for real-time PCR, performed using a 25 µL reaction volume in a silver block Mastercycler® ep realplex 4S (Eppendorf, Hamburg, Germany) with the following conditions: 95° C., 10 minutes, 1 cycle; 95° C., 15 seconds and 60° C., 1 minute, 40 cycles. For the determination of melting curves, the following conditions were used: 95° C., 15 seconds, 60° C., 15 seconds, 60° C. to 95° C. at 26% ramp, 20 minutes and 95° C., 15 seconds, 1 cycle. Reactions for each biological replicate were conducted in technical duplicates.

Real-time qRT-PCR data extraction and initial analysis were performed using the Mastercycler® ep realplex software (Eppendorf, Hamburg, Germany). A manual threshold of 200 and an automatic baseline were applied to obtain the threshold cycle (Ct) for each measurement. Relative quantification of the target genes of interest was carried out using the GenEx 4.3.6 software (MultiD Analyses AB, Sweden). The data analysis took into account calculations using multiple housekeeping genes, in which the expression levels of target genes were normalised to the geometric mean of the three most stable reference genes, chosen from the five tested using the geNorm (Vandesompele et al., 2002) and Normfinder (Andersen et al., 2004) analyses available in the GenEx 4.3.6 software (MultiD Analyses AB, Sweden).

TABLE 2

Target and reference genes selected for the real-time qRT-PCR validation of the microarray datasets for whole fruit fly larvae and larval fat bodies (Experiment 4)

| Gene Symbol | Gene Name | RT² Profiler™ PCR Arrays Gene Catalogue Number |
|---|---|---|
| *Target Genes for Whole Fruit Fly Larvae* | | |
| Lcp65Ab1 | CG32400 gene product from transcript CG32400-RA | PPD11246A |
| Lcp9 | Larval cuticle protein 9 | PPD05819A |
| CG7296 | CG7296 gene product from transcript CG7296-RB | PPD02913A |
| CG9090 | CG9090 gene product from transcript CG9090-RA | PPD05260A |
| CG17105 | CG17105 gene product from transcript CG17105-RA | PPD02910A |
| TpnC47D | Troponin C at 47D | PPD04323A |
| Lcp65Ac | CG6956 gene product from transcript CG6956-RA | PPD06425A |
| CG11300 | CG11300 gene product from transcript CG11300-RA | PPD05649A |
| Ac76E | Adenylyl cyclase 76E | PPD07685A |
| CG14258 | CG14258 gene product from transcript CG14258-RA | PPD10306A |
| CG40002 | CG40002 gene product from transcript CG40002-RA | PPD13019A |
| Sodh2 | Sorbitol dehydrogenase 2 | PPD08672A |
| CG14292 | CG14292 gene product from transcript CG14292-RA | PPD09454A |
| ObstG | Obstructor G | PPD06966A |
| CG17751 | CG17751 gene product from transcript CG17751-RB | PPD09509A |
| CG10514 | CG10514 gene product from transcript CG10514-RA | PPD10130A |
| CG17826 | CG17826 gene product from transcript CG17826-RA | PPD06965A |
| ImpE1 | Ecdysone-inducible gene E1 | PPD11111A |
| CG17181 | CG17181 gene product from transcript CG17181-RA | PPD05907A |
| CG4950 | CG4950 gene product from transcript CG4950-RC | PPD07332A |
| *Target Genes for Larval Fat Bodies* | | |
| CG17105 | CG17105 gene product from transcript CG17105-RA | PPD02910A |
| Hsp70Bb | Heat shock protein 70Bb | PPD11262A |
| Hsp70Bbb | CG5834 gene product from transcript CG5834 RA | PPD11327A |
| Hsp70Ab | Heat shock protein 70Ab | PPD11030A |
| CG34244 | CG34244 gene product from transcript CG34244-RB | PPD13444A |
| Hsp70Ba | Heat shock protein 70Ba | PPD11031A |
| Hsp68 | Heat shock protein 68 | PPD09955A |
| Dro5 | Drosomycin 5 | PPD06177A |
| CG16704 | CG16704 gene product from transcript CG16704-RA | PPD02185A |
| CG13641 | CG13641 gene product from transcript CG13641-RA | PPD10059A |
| Nplp4 | Neuropeptide-like precursor 4 | PPD11384A |
| CG16713 | CG16713 gene product from transcript CG16713-RA | PPD02187A |
| CG6870 | CG6870 gene product from transcript CG6870-RA | PPD03423A |
| CG8157 | CG8157 gene product from transcript CG8157-RA | PPD04762A |
| CG7567 | CG7567 gene product from transcript CG7567-RA | PPD10487A |
| CG7017 | CG7017 gene product from transcript CG7017-RB | PPD07715A |
| CG14945 | CG14945 gene product from transcript CG14945-RB | PPD03040A |
| CG5404 | CG5404 gene product from transcript CG5404-RA | PPD09154A |
| Slbo | Slow border cells | PPD05752A |
| CG8492 | CG8492 gene product from transcript CG8492-RD | PPD06560A |
| *Reference Genes for Whole Fruit Fly Larvae and Larval Fat Bodies* | | |
| CG15117 | CG15117 gene product from transcript CG15117-RA | PPD05171A |
| CG17266 | CG17266 gene product from transcript CG17266-RA | PPD03818A |
| Cyp33 | Cyclophilin 33 | PPD04989A |
| RpL13A | Ribosomal protein L13A | PPD08119B |

The 40 target genes were selected for qRT-PCR as they were differentially expressed between the control and treatment groups ($p < 0.05$) and showed the highest fold changes, based on the microarray analysis carried out. Five candidate reference genes were also chosen for expression stability testing between the control and PFJ supplemented groups, with the three most stable ones being finally selected for relative quantification of the target genes in each of the datasets for whole fruit fly larvae and larval fat bodies.

For the whole larvae dataset, CG17266, Cyp33 and RpLP0/CG15117, reference genes were used to normalise the target genes. On the other hand, for the fat bodies dataset, CG15117, Cyp33 and RpLP0 reference genes were used. Statistical analysis on the relative gene expression levels obtained was conducted by using the two-tailed unpaired Student's t-test in the Microsoft Excel software (Microsoft Corporation, Redmond, Wash.) and differences with p values <0.05 after correction for multiple testing using the Benjamini-Hochberg method at a false discovery rate of 0.05 (McDonald 2014) were considered statistically significant.

Results

Microarray gene expression analysis on whole fruit fly larvae revealed that compared to controls, 127 genes were up-regulated while 67 were down-regulated in PFJ supplemented larvae, when cut off values of fold changes >|1.30| and p values <0.05 were applied (Table 6).

TABLE 6

List of genes significantly regulated by PFJ in whole fruit fly larvae (Experiment 4)

| Gene Symbol | Description | ANOVA P-Value | Fold Change |
|---|---|---|---|
| | Genes Up-Regulated in Whole Fruit Fly Larvae | | |
| Lcp65Ab1 | CG32400 gene product from transcript CG32400-RA | 0.0451 | 12.61 |
| Lcp65Ab2 | CG18773 gene product from transcript CG18773-RA | 0.0451 | 12.61 |
| Lcp9 | Larval cuticle protein 9 | 0.0296 | 6.64 |
| CG7296 | CG7296 gene product from transcript CG7296-RB | 0.0433 | 5.80 |
| CG9090 | CG9090 gene product from transcript CG9090-RA | 0.0251 | 4.10 |
| CG17105 | CG17105 gene product from transcript CG17105-RA | 0.0314 | 3.73 |
| TpnC47D | Troponin C at 47D | 0.0368 | 3.42 |
| Lcp65Ac | CG6956 gene product from transcript CG6956-RA | 0.0409 | 2.87 |
| CG11300 | CG11300 gene product from transcript CG11300-RA | 0.0442 | 2.78 |
| Ac76E | Adenylyl cyclase 76E | 0.0452 | 2.75 |
| CG14258 | CG14258 gene product from transcript CG14258-RA | 0.0304 | 2.45 |
| CG40002 | CG40002 gene product from transcript CG40002-RA | 0.0283 | 2.42 |
| Sodh2 | Sorbitol dehydrogenase 2 | 0.0226 | 2.41 |
| CG14292 | CG14292 gene product from transcript CG14292-RA | 0.0105 | 2.40 |
| ObstG | Obstructor G | 0.0466 | 2.29 |
| CG17751 | CG17751 gene product from transcript CG17751-RB | 0.0095 | 2.16 |
| CG10514 | CG10514 gene product from transcript CG10514-RA | 0.0495 | 2.14 |
| CG17826 | CG17826 gene product from transcript CG17826-RA | 0.0195 | 2.13 |
| CR40572 | Ribosomal RNA | 0.0161 | 2.09 |
| Salt | Salty dog | 0.0168 | 2.09 |
| JhI26 | Juvenile hormone-inducible protein 26 | 0.0279 | 2.08 |
| Actn; Usp | Alpha actinin; ultraspiracle | 0.0262 | 1.98 |
| CG10513 | CG10513 gene product from transcript CG10513-RB | 0.0208 | 1.97 |
| CG9451 | CG9451 gene product from transcript CG9451-RB | 0.0479 | 1.94 |
| CG8353 | CG8353 gene product from transcript CG8353-RB | 0.0415 | 1.92 |
| Ea | Easter | 0.0161 | 1.91 |
| Nha2 | Na+/H+ hydrogen antiporter 2 | 0.0435 | 1.84 |
| CG17029 | CG17029 gene product from transcript CG17029-RB | 0.0050 | 1.83 |
| CG7224 | CG7224 gene product from transcript CG7224-RB | 0.0474 | 1.83 |
| CG34445 | CG34445 gene product from transcript CG34445-RA | 0.0235 | 1.81 |
| CG43341 | CG43341 gene product from transcript CG43341-RA | 0.0390 | 1.80 |
| Peritrophin-A | Peritrophin-A | 0.0417 | 1.77 |
| CG4302 | CG4302 gene product from transcript CG4302-RA | 0.0302 | 1.76 |
| CG15282 | CG15282 gene product from transcript CG15282-RA | 0.0420 | 1.76 |
| CG9498 | CG9498 gene product from transcript CG9498-RA | 0.0385 | 1.75 |
| CG11368 | CG11368 gene product from transcript CG11368-RA | 0.0255 | 1.73 |
| Scp2 | Sarcoplasmic calcium-binding protein 2 | 0.0357 | 1.73 |
| CG34120 | CG34120 gene product from transcript CG34120-RC | 0.0427 | 1.73 |
| CG10433 | CG10433 gene product from transcript CG10433-RA | 0.0039 | 1.72 |
| CG32564 | CG32564 gene product from transcript CG32564-RA | 0.0250 | 1.72 |
| CG14273 | CG14273 gene product from transcript CG14273-RA | 0.0025 | 1.70 |
| CG11050 | CG11050 gene product from transcript CG11050-RA | 0.0070 | 1.70 |
| CG17108 | CG17108 gene product from transcript CG17108-RA | 0.0015 | 1.69 |
| Mlc1 | Myosin alkali light chain 1 | 0.0249 | 1.68 |
| ND4; ND4L | NADH dehydrogenase subunit 4; NADH dehydrogenase subunit 4L | 0.0289 | 1.68 |
| CG3835 | CG3835 gene product from transcript CG3835-RC | 0.0161 | 1.65 |
| CG41128 | CG41128 gene product from transcript CG41128-RB | 0.0410 | 1.65 |
| ND1 | NADH dehydrogenase subunit 1 | 0.0146 | 1.63 |
| CG7798 | CG7798 gene product from transcript CG7798-RA | 0.0311 | 1.61 |
| CG32213 | CG32213 gene product from transcript CG32213-RB | 0.0056 | 1.60 |
| CG17698 | CG17698 gene product from transcript CG17698-RF | 0.0096 | 1.60 |
| CG17734 | CG17734 gene product from transcript CG17734-RA | 0.0206 | 1.60 |
| CG15414 | CG15414 gene product from transcript CG15414-RA | 0.0306 | 1.60 |
| CG17715 | CG17715 gene product from transcript CG17715-RG | 0.0406 | 1.60 |
| Mlc2 | Myosin light chain 2 | 0.0322 | 1.59 |
| CG12206 | CG12206 gene product from transcript CG12206-RA | 0.0042 | 1.58 |
| CG6020 | CG6020 gene product from transcript CG6020-RA | 0.0209 | 1.58 |
| CG7206 | CG7206 gene product from transcript CG7206-RB | 0.0428 | 1.55 |
| CG3621 | CG3621 gene product from transcript CG3621-RA | 0.0091 | 1.54 |
| Gpo1 | Glycerophosphate oxidase 1 | 0.0415 | 1.54 |
| CG9836 | CG9836 gene product from transcript CG9836-RA | 0.0115 | 1.52 |
| GstE1 | Glutathione S transferase E1 | 0.0362 | 1.52 |
| CG14630 | CG14630 gene product from transcript CG14630-RA | 0.0409 | 1.52 |
| Acox57D-p | Acyl-Coenzyme A oxidase at 57D proximal | 0.0240 | 1.51 |
| CG10877 | CG10877 gene product from transcript CG10877-RA | 0.0305 | 1.51 |
| Dnr1 | Defense repressor 1 | 0.0030 | 1.50 |
| CG6330 | CG6330 gene product from transcript CG6330-RB | 0.0186 | 1.50 |
| CG17167 | CG17167 gene product from transcript CG17167-RD | 0.0400 | 1.50 |
| CG34301 | CG34301 gene product from transcript CG34301-RA | 0.0016 | 1.49 |
| CG12567 | CG12567 gene product from transcript CG12567-RF | 0.0271 | 1.48 |
| CG9331 | CG9331 gene product from transcript CG9331-RF | 0.0283 | 1.48 |
| Obp83g | Odorant-binding protein 83g | 0.0283 | 1.48 |

TABLE 6-continued

List of genes significantly regulated by PFJ in whole fruit fly larvae (Experiment 4)

| Gene Symbol | Description | ANOVA P-Value | Fold Change |
|---|---|---|---|
| CG11349 | CG11349 gene product from transcript CG11349-RB | 0.0024 | 1.47 |
| CG34043 | CG34043 gene product from transcript CG34043-RB | 0.0062 | 1.47 |
| RFeSP | Rieske iron-sulfur protein | 0.0362 | 1.47 |
| CG3362 | CG3362 gene product from transcript CG3362-RA | 0.0232 | 1.46 |
| Sp212 | Serine-peptidase 212 | 0.0260 | 1.44 |
| Ucrh | Ubiquinol-cytochrome C reductase complex 11 kDa protein | 0.0212 | 1.43 |
| Cpr78Ca | Cuticular protein 78Ca | 0.0317 | 1.43 |
| Amph | Amphiphysin | 0.0340 | 1.43 |
| snoRNA:Psi28S-3305b | ncRNA | 0.0392 | 1.43 |
| betaInt-nu | beta[nu] integrin | 0.0398 | 1.43 |
| Peritrophin-15a | CG17814 gene product from transcript CG17814-RA | 0.0457 | 1.43 |
| Mthl14 | Methuselah-like 14 | 0.0354 | 1.42 |
| CG17273 | CG17273 gene product from transcript CG17273-RA | 0.0406 | 1.42 |
| CG17109 | CG17109 gene product from transcript CG17109-RB | 0.0415 | 1.42 |
| ND5 | NADH dehydrogenase subunit 5 | 0.0420 | 1.42 |
| CG6904 | CG6904 gene product from transcript CG6904-RC | 0.0116 | 1.41 |
| Oatp58Da | Organic anion transporting polypeptide 58 Da | 0.0218 | 1.41 |
| snoRNA:Psi28S-3316c | ncRNA | 0.0063 | 1.40 |
| GluRIIC | Glutamate receptor IIC | 0.0153 | 1.40 |
| WupA | Wings up A | 0.0316 | 1.40 |
| CG32230 | CG32230 gene product from transcript CG32230-RC | 0.0462 | 1.40 |
| CanA1 | Calcineurin A1 | 0.0255 | 1.39 |
| Proc-R | Proctolin receptor | 0.0290 | 1.39 |
| CG13003 | CG13003 gene product from transcript CG13003-RC | 0.0294 | 1.39 |
| ATP8 | ATP synthase F0 subunit 8 | 0.0335 | 1.39 |
| SesB | Stress-sensitive B | 0.0056 | 1.38 |
| CG5541; Be | CG5541 gene product from transcript CG5541-RA; ben | 0.0293 | 1.38 |
| Irk3 | Inwardly rectifying potassium channel 3 | 0.0211 | 1.37 |
| Rac2 | CG8556 gene product from transcript CG8556-RB | 0.0285 | 1.37 |
| Tx | Taxi | 0.0327 | 1.37 |
| Cyp317a1 | CG17453 gene product from transcript CG17453-RA | 0.0368 | 1.37 |
| CG11447 | CG11447 gene product from transcript CG11447-RA | 0.0053 | 1.36 |
| CG3744 | CG3744 gene product from transcript CG3744-RG | 0.0081 | 1.36 |
| Rab9 | CG9994 gene product from transcript CG9994-RA | 0.0138 | 1.36 |
| MYPT-75D | CG6896 gene product from transcript CG6896-RB | 0.0033 | 1.35 |
| Gyc76C; CG42637 | Guanylyl cyclase at 76C; CG42637 gene product from transcript CG42637-RB | 0.0492 | 1.35 |
| Gyc76C; CG42637 | Guanylyl cyclase at 76C; CG42637 gene product from transcript CG42637-RB | 0.0492 | 1.35 |
| CG34228 | CG34228 gene product from transcript CG34228-RA | 0.0172 | 1.34 |
| snoRNA:Me28S-A982a | ncRNA | 0.0386 | 1.34 |
| CG12170 | CG12170 gene product from transcript CG12170-RA | 0.0094 | 1.33 |
| Ndae1 | Na+-driven anion exchanger 1 | 0.0226 | 1.33 |
| SdhA | Succinate dehydrogenase A | 0.0305 | 1.33 |
| Rho | Rhomboid | 0.0409 | 1.33 |
| CG30491 | CG30491 gene product from transcript CG30491-RA | 0.0440 | 1.33 |
| CG11889; CG11891 | CG11889 gene product from transcript CG11889-RA; CG11891 gene product from transcript CG11891-RD | 0.0023 | 1.32 |
| CG11889; CG11891 | CG11889 gene product from transcript CG11889-RA; CG11891 gene product from transcript CG11891-RD | 0.0023 | 1.32 |
| L(1)G0230 | Lethal (1) G0230 | 0.0122 | 1.32 |
| CG17691 | CG17691 gene product from transcript CG17691-RC | 0.0165 | 1.32 |
| CG13377 | CG13377 gene product from transcript CG13377-RB | 0.0378 | 1.32 |
| CG4839 | CG4839 gene product from transcript CG4839-RA | 0.0014 | 1.31 |
| PhKgamma | Phosphorylase kinase gamma | 0.0382 | 1.31 |
| Ptp4E | Protein tyrosine phosphatase 4E | 0.0415 | 1.31 |
| Esp | Epidermal stripes and patches | 0.0430 | 1.31 |
| AlphaTub67C | Alpha-tubulin at 67C | 0.0172 | 1.30 |
| CG17600 | CG17600 gene product from transcript CG17600-RA | 0.0250 | 1.30 |

Genes Down-Regulated in Whole Fruit Fly Larvae

| L(1)sc | Lethal of scute | 0.0177 | −1.30 |
| CG3163 | CG3163 gene product from transcript CG3163-RA | 0.0209 | −1.30 |
| Ush | U-shaped | 0.0271 | −1.30 |
| CG40172 | CG40172 gene product from transcript CG40172-RB | 0.0392 | −1.30 |
| CG8112 | CG8112 gene product from transcript CG8112-RA | 0.0485 | −1.30 |
| CG7156 | CG7156 gene product from transcript CG7156-RB | 0.0010 | −1.31 |
| Nab2 | CG5720 gene product from transcript CG5720-RA | 0.0068 | −1.31 |
| RhoGAP19D | CG1412 gene product from transcript CG1412-RB | 0.0082 | −1.31 |

TABLE 6-continued

List of genes significantly regulated by PFJ in whole fruit fly larvae (Experiment 4)

| Gene Symbol | Description | ANOVA P-Value | Fold Change |
|---|---|---|---|
| CG12056 | CG12056 gene product from transcript CG12056-RA | 0.0223 | −1.31 |
| Tor | Target of rapamycin | 0.0225 | −1.31 |
| Pdm3 | Pou domain motif 3 | 0.0238 | −1.31 |
| CG9318 | CG9318 gene product from transcript CG9318-RB | 0.0387 | −1.31 |
| Rux | Roughex | 0.0208 | −1.32 |
| CG14194 | CG14194 gene product from transcript CG14194-RA | 0.0497 | −1.32 |
| CG14851 | CG14851 gene product from transcript CG14851-RA | 0.0363 | −1.33 |
| Hppy | Happyhour | 0.0386 | −1.33 |
| snoRNA:Or-CD1 | ncRNA | 0.0417 | −1.33 |
| CG30015 | CG30015 gene product from transcript CG30015-RA | 0.0497 | −1.33 |
| CG13423 | CG13423 gene product from transcript CG13423-RA | 0.0100 | −1.34 |
| Liprin-gamma | CG11206 gene product from transcript CG11206-RA | 0.0255 | −1.34 |
| Cv-d | Crossveinless d | 0.0414 | −1.34 |
| CG11069 | CG11069 gene product from transcript CG11069-RA | 0.0025 | −1.35 |
| LanB2 | Laminin B2 | 0.0188 | −1.36 |
| CG4783 | CG4783 gene product from transcript CG4783-RA | 0.0223 | −1.36 |
| mir-4985; MIMAT0020222; MIMAT0020221; MI0017771 | mir-4985 stem loop | 0.0316 | −1.36 |
| Abi | Abelson interacting protein | 0.0470 | −1.36 |
| CG4764 | CG4764 gene product from transcript CG4764-RA | 0.0111 | −1.37 |
| Lcch3 | Ligand-gated chloride channel homolog 3 | 0.0233 | −1.37 |
| CG4914 | CG4914 gene product from transcript CG4914-RA | 0.0423 | −1.37 |
| Tsp | Thrombospondin | 0.0002 | −1.38 |
| CG9664 | CG9664 gene product from transcript CG9664-RA | 0.0027 | −1.38 |
| CG5446 | CG5446 gene product from transcript CG5446-RC | 0.0190 | −1.38 |
| CG3226 | CG3226 gene product from transcript CG3226-RA | 0.0277 | −1.38 |
| Drsl1 | Drosomycin-like 1 | 0.0064 | −1.39 |
| mir-4947; MIMAT0020157; MI0017733 | mir-4947 stem loop | 0.0403 | −1.39 |
| CG7133 | CG7133 gene product from transcript CG7133-RA | 0.0220 | −1.40 |
| BetaTub60D | Beta-tubulin at 60D | 0.0088 | −1.41 |
| BetaNACtes4 | CG18313 gene product from transcript CG18313-RA | 0.0263 | −1.41 |
| Sec6 | CG5341 gene product from transcript CG5341-RA | 0.0424 | −1.42 |
| Let-7-C; mir-125; MIMAT0000397; MI0000417 | Let-7-complex; mir-125 stem loop | 0.0324 | −1.43 |
| CG34296 | CG34296 gene product from transcript CG34296-RA | 0.0486 | −1.44 |
| Tep1 | Thioester-containing protein 1 | 0.0104 | −1.46 |
| CG31368 | CG31368 gene product from transcript CG31368-RD | 0.0073 | −1.47 |
| CG30089 | CG30089 gene product from transcript CG30089-RA | 0.0316 | −1.48 |
| Sesn | Sestrin | 0.0239 | −1.49 |
| Mur89F | Mucin related 89F | 0.0486 | −1.50 |
| Sgs4 | Salivary gland secretion 4 | 0.0368 | −1.52 |
| Mthl2 | Methuselah-like 2 | 0.0018 | −1.53 |
| NimA | Nimrod A | 0.0053 | −1.53 |
| CG5509 | CG5509 gene product from transcript CG5509-RA | 0.0198 | −1.54 |
| CG31407 | CG31407 gene product from transcript CG31407-RA | 0.0472 | −1.54 |
| CG42566 | CG42566 gene product from transcript CG42566-RA | 0.0345 | −1.56 |
| Rab9Fa | Rab at 9Fa | 0.0207 | −1.59 |
| snRNA:U1:95Cc | Small nuclear RNA U1 at 95Cc | 0.0480 | −1.59 |
| nAcRalpha-30D | Nicotinic acetylcholine receptor alpha 30D | 0.0304 | −1.60 |
| Tok | Tolkin | 0.0484 | −1.64 |
| Dys; snoRNA:Me18S-A1374 | Dystrophin; ncRNA | 0.0104 | −1.65 |
| Mical | Molecule interacting with CasL | 0.0482 | −1.65 |
| LanA | Laminin A | 0.0213 | −1.68 |
| Pnr | Pannier | 0.0399 | −1.68 |
| CG31320 | CG31320 gene product from transcript CG31320-RA | 0.0356 | −1.75 |
| Spn43Aa | Serpin 43Aa | 0.0283 | −1.78 |
| CG42666 | CG42666 gene product from transcript CG42666-RG | 0.0354 | −1.78 |
| CG32437 | CG32437 gene product from transcript CG32437-RA | 0.0244 | −1.85 |
| ImpE1 | Ecdysone-inducible gene E1 | 0.0495 | −2.05 |
| CG17181 | CG17181 gene product from transcript CG17181-RA | 0.0090 | −2.24 |
| CG4950 | CG4950 gene product from transcript CG4950-RC | 0.0262 | −2.53 |

Functional enrichment analysis of these differentially expressed genes on gene ontologies (biological processes) using the GO-Elite software showed that transport and metabolic processes were up-regulated, while development and morphogenesis processes were down-regulated.

TABLE 7

List of gene ontologies (biological processes) significantly regulated by PFJ in whole fruit fly larvae (Experiment 4)

| Ontology ID | Ontology Name | Number of Genes Changed | Percent Changed | Z Score | Permuted p Value |
|---|---|---|---|---|---|
| Gene Ontologies (Biological Processes) Up-Regulated in Whole Fruit Fly Larvae | | | | | |
| GO: 0006091 | Generation of precursor metabolites & energy | 10 | 8.4034 | 8.3785 | 0.0000 |
| GO: 0006820 | Anion transport | 4 | 8.8889 | 5.4687 | 0.0000 |
| GO: 0007629 | Flight behaviour | 3 | 15.7895 | 6.6376 | 0.0005 |
| GO: 0055086 | Nucleobase, nucleoside & nucleotide metabolic process | 7 | 3.7433 | 3.9410 | 0.0005 |
| GO: 0005976 | Polysaccharide metabolic process | 6 | 4.5455 | 4.2537 | 0.0015 |
| GO: 0006818 | Hydrogen transport | 3 | 5.4545 | 3.4290 | 0.0105 |
| GO: 0042592 | Homeostatic process | 5 | 2.8571 | 2.5974 | 0.0165 |
| GO: 0006793 | Phosphorus metabolic process | 8 | 1.9370 | 2.0800 | 0.0315 |
| GO: 0044282 | Small molecule catabolic process | 4 | 3.0303 | 2.4565 | 0.0335 |
| GO: 0042048 | Olfactory behaviour | 3 | 3.4884 | 2.4160 | 0.0435 |
| GO: 0016192 | Vesicle-mediated transport | 5 | 2.2624 | 2.0087 | 0.0450 |
| GO: 0051186 | Cofactor metabolic process | 3 | 2.9412 | 2.0635 | 0.0470 |
| Gene Ontologies (Biological Processes) Down-Regulated in Whole Fruit Fly Larvae | | | | | |
| GO: 0009653 | Anatomical structure morphogenesis | 12 | 1.6371 | 4.7906 | 0.0000 |
| GO: 0048513 | Organ development | 9 | 1.8109 | 4.4779 | 0.0000 |
| GO: 0007411 | Axon guidance | 4 | 2.3392 | 3.6029 | 0.0040 |
| GO: 0044456 | Synapse part | 3 | 2.8571 | 3.5940 | 0.0095 |
| GO: 0009888 | Tissue development | 3 | 2.3438 | 3.1182 | 0.0130 |
| GO: 0051128 | Regulation of cellular component organisation | 5 | 1.3514 | 2.5234 | 0.0170 |
| GO: 0051704 | Multi-organism process | 4 | 1.5873 | 2.6247 | 0.0215 |
| GO: 0040008 | Regulation of growth | 3 | 2.0000 | 2.7592 | 0.0240 |
| GO: 0044421 | Extracellular region part | 4 | 1.5444 | 2.5596 | 0.0255 |
| GO: 0044425 | Membrane part | 12 | 0.8186 | 2.1042 | 0.0280 |
| GO: 0032879 | Regulation of localisation | 3 | 1.8868 | 2.6317 | 0.0290 |
| GO: 0022610 | Biological adhesion | 3 | 1.7045 | 2.4147 | 0.0290 |
| GO: 0016044 | Cellular membrane organisation | 4 | 1.2658 | 2.1000 | 0.0490 |

Regulatory network analysis using the Pathway Studio software (Elsevier B.V., Amsterdam, Netherlands) revealed that for the whole fruit fly larvae data, 35 out of the 127 up-regulated genes could be mapped onto human orthologues, but no relationships between these mapped genes could be identified. On the other hand, 22 out of 67 down-regulated genes could be mapped onto human orthologues, and 6 relationships were identified between the mapped genes, with 15 unconnected entities removed (FIG. 1A). Among the genes plotted in the regulatory network, the MTOR (mechanistic target of rapamycin) or Tor (target of rapamycin) gene appeared most important. The ImpE1 (ecdysone-inducible gene E1) gene was also found significantly down-regulated in whole fruit fly larvae supplemented with PFJ.

Using a similar cut off, microarray gene expression analysis on larval fat bodies showed that 161 genes were up-regulated, while 84 genes were down-regulated following PFJ supplementation, including various heat shock proteins (Table 8).

TABLE 8

List of genes significantly regulated by PFJ in larval fat bodies (Experiment 4)

| Gene Symbol | Description | ANOVA P-Value | Fold Change |
|---|---|---|---|
| Genes Up-Regulated in Larval Fat Bodies | | | |
| CG17105 | CG17105 gene product from transcript CG17105-RA | 0.0427 | 18.16 |
| Hsp70Bb | Heat shock protein 70Bb | 0.0474 | 8.69 |
| Hsp70Bbb | CG5834 gene product from transcript CG5834 RA | 0.0192 | 6.15 |
| Hsp70Ab | Heat shock protein 70Ab | 0.0198 | 4.99 |
| CG34244 | CG34244 gene product from transcript CG34244-RB | 0.0110 | 4.59 |
| Hsp70Ba | Heat shock protein 70Ba | 0.0416 | 4.52 |
| Hsp68 | Heat shock protein 68 | 0.0335 | 4.36 |
| Dro5 | Drosomycin 5 | 0.0123 | 4.04 |
| CG16704 | CG16704 gene product from transcript CG16704-RA | 0.0251 | 3.62 |
| CG13641 | CG13641 gene product from transcript CG13641-RA | 0.0065 | 3.58 |
| Nplp4 | Neuropeptide-like precursor 4 | 0.0266 | 3.33 |
| CG16713 | CG16713 gene product from transcript CG16713-RA | 0.0017 | 3.29 |
| Hsp70Bc | Heat shock protein 70Bc | 0.0100 | 3.29 |
| CG6870 | CG6870 gene product from transcript CG6870-RA | 0.0399 | 3.29 |
| CG8157 | CG8157 gene product from transcript CG8157-RA | 0.0295 | 3.24 |
| CG32249 | CG32249 gene product from transcript CG32249-RB | 0.0127 | 3.05 |
| CG42500 | CG42500 gene product from transcript CG42500-RB | 0.0074 | 3.02 |
| CG3397 | CG3397 gene product from transcript CG3397-RA | 0.0150 | 2.87 |
| Reg2 | Rhythmically expressed gene 2 | 0.0354 | 2.72 |
| CG16926 | CG16926 gene product from transcript CG16926-RA | 0.0059 | 2.69 |
| CG15369 | CG15369 gene product from transcript CG15369-RA | 0.0347 | 2.68 |
| CG7924 | CG7924 gene product from transcript CG7924-RA | 0.0449 | 2.65 |
| CG13890 | CG13890 gene product from transcript CG13890-RA | 0.0398 | 2.62 |
| CG5773 | CG5773 gene product from transcript CG5773-RA | 0.0163 | 2.52 |
| CG10592 | CG10592 gene product from transcript CG10592-RA | 0.0447 | 2.45 |
| MESK4; | Misexpression suppressor of KSR 4; | 0.0380 | 2.40 |
| CG31274 | CG31274 gene product from transcript CG31274-RA | | |
| E | Ebony | 0.0284 | 2.34 |
| Ade5 | CG3989 gene product from transcript CG3989 RB | 0.0030 | 2.26 |
| Prat2 | Phosphoribosylamidotransferase 2 | 0.0003 | 2.24 |
| CG33493 | CG33493 gene product from transcript CG33493-RB | 0.0099 | 2.22 |
| Cpr67B | Cuticular protein 67B | 0.0225 | 2.21 |
| CG13606 | CG13606 gene product from transcript CG13606-RB | 0.0394 | 2.20 |
| Ade3 | Adenosine 3 | 0.0491 | 2.18 |
| CG15772 | CG15772 gene product from transcript CG15772-RA | 0.0150 | 2.17 |
| Hn | Henna | 0.0499 | 2.17 |
| CG8369 | CG8369 gene product from transcript CG8369-RC | 0.0382 | 2.16 |
| Oat | Ornithine aminotransferase precursor | 0.0052 | 2.13 |
| CG6762 | CG6762 gene product from transcript CG6762-RD | 0.0099 | 2.11 |
| CG13962 | CG13962 gene product from transcript CG13962-RB | 0.0482 | 2.10 |
| CG7322 | CG7322 gene product from transcript CG7322-RA | 0.0338 | 2.08 |
| CG9509 | CG9509 gene product from transcript CG9509-RA | 0.0018 | 2.05 |
| AttC | Attacin C | 0.0156 | 2.05 |
| Pgi | Phosphoglucose isomerase | 0.0447 | 2.02 |
| CG6639 | CG6639 gene product from transcript CG6639-RA | 0.0100 | 2.01 |
| CG31266 | CG31266 gene product from transcript CG31266-RB | 0.0438 | 2.01 |
| CG1236 | CG1236 gene product from transcript CG1236-RA | 0.0208 | 2.00 |
| Cyp309a1 | CG9964 gene product from transcript CG9964-RC | 0.0244 | 1.95 |
| Tal | CG2827 gene product from transcript CG2827-RA | 0.0294 | 1.94 |
| CG34206 | CG34206 gene product from transcript CG34206-RA | 0.0493 | 1.94 |
| Arg | Arginase | 0.0404 | 1.92 |
| UK114 | CG15261 gene product from transcript CG15261-RB | 0.0098 | 1.91 |
| CG12338 | CG12338 gene product from transcript CG12338-RA | 0.0215 | 1.90 |
| CG43166 | CG43166 gene product from transcript CG43166-RA | 0.0449 | 1.90 |
| CG32276 | CG32276 gene product from transcript CG32276-RB | 0.0150 | 1.89 |
| CG18607 | CG18607 gene product from transcript CG18607-RA | 0.0396 | 1.89 |
| CG31778 | CG31778 gene product from transcript CG31778-RA | 0.0011 | 1.86 |
| Eip55E | CG5345 gene product from transcript CG5345-RA | 0.0041 | 1.86 |
| snoRNA: Me28S-C788a | ncRNA | 0.0069 | 1.86 |
| Hsp26 | Heat shock protein 26 | 0.0244 | 1.84 |
| CG5044 | CG5044 gene product from transcript CG5044-RB | 0.0146 | 1.80 |
| nAcRbeta-21C | Nicotinic acetylcholine receptor beta 21C | 0.0384 | 1.80 |
| CG18666 | CG18666 gene product from transcript CG18666-RA | 0.0042 | 1.79 |
| CG8586 | CG8586 gene product from transcript CG8586-RA | 0.0199 | 1.79 |
| CG32751 | CG32751 gene product from transcript CG32751-RA | 0.0290 | 1.79 |
| Vago | CG2081 gene product from transcript CG2081-RC | 0.0463 | 1.77 |
| CG5577 | CG5577 gene product from transcript CG5577-RA | 0.0201 | 1.76 |
| CG10799 | CG10799 gene product from transcript CG10799-RA | 0.0322 | 1.76 |
| TotA | TurandotA | 0.0180 | 1.75 |
| Nxt1 | NTF2-related export protein 1 | 0.0421 | 1.74 |
| Mal-B2 | Maltase B2 | 0.0005 | 1.73 |
| Regucalcin | CG1803 gene product from transcript CG1803-RA | 0.0381 | 1.73 |

TABLE 8-continued

List of genes significantly regulated by PFJ in larval fat bodies (Experiment 4)

| Gene Symbol | Description | ANOVA P-Value | Fold Change |
|---|---|---|---|
| CG2233 | CG2233 gene product from transcript CG2233-RA | 0.0080 | 1.70 |
| CG1773 | CG1773 gene product from transcript CG1773-RA | 0.0176 | 1.69 |
| Psf2 | CG18013 gene product from transcript CG18013-RC | 0.0192 | 1.69 |
| CG10527 | CG10527 gene product from transcript CG10527-RA | 0.0090 | 1.68 |
| Cyp4d2 | Cytochrome P450-4d2 | 0.0339 | 1.67 |
| CecB | Cecropin B | 0.0081 | 1.66 |
| Su(Ste): CR42422 | ncRNA | 0.0362 | 1.66 |
| CG33470; IM10 | CG33470 gene product from transcript CG33470-RA; Immune induced molecule 10 | 0.0321 | 1.65 |
| CG42823 | CG42823 gene product from transcript CG42823-RA | 0.0484 | 1.65 |
| Pcd | Pterin-4a-carbinolamine dehydratase | 0.0132 | 1.64 |
| CG10031 | CG10031 gene product from transcript CG10031-RA | 0.0144 | 1.63 |
| CG17292 | CG17292 gene product from transcript CG17292-RB | 0.0239 | 1.60 |
| CG34230 | CG34230 gene product from transcript CG34230-RA | 0.0332 | 1.60 |
| CG43208 | CG43208 gene product from transcript CG43208-RA | 0.0341 | 1.60 |
| CG3505 | CG3505 gene product from transcript CG3505-RA | 0.0000 | 1.57 |
| CG33138 | CG33138 gene product from transcript CG33138-RA | 0.0159 | 1.56 |
| NimB2 | Nimrod B2 | 0.0388 | 1.56 |
| DptB | Diptericin B | 0.0292 | 1.53 |
| CG10672 | CG10672 gene product from transcript CG10672-RA | 0.0294 | 1.53 |
| CG34166 | CG34166 gene product from transcript CG34166-RA | 0.0366 | 1.53 |
| CG6067 | CG6067 gene product from transcript CG6067-RA | 0.0398 | 1.52 |
| Lcp65Ae | CG10529 gene product from transcript CG10529-RA | 0.0151 | 1.51 |
| mir-2493; MIMAT0012200; MIMAT0012201; MI0011582 | mir-2493 stem loop | 0.0162 | 1.51 |
| CG14207 | CG14207 gene product from transcript CG14207-RB | 0.0358 | 1.50 |
| AlCR2 | Allatostatin C receptor 2 | 0.0443 | 1.50 |
| Trh | Tryptophan hydroxylase | 0.0238 | 1.49 |
| snoRNA: Me28S-U1848 | ncRNA | 0.0347 | 1.49 |
| CG43236 | CG43236 gene product from transcript CG43236-RA | 0.0370 | 1.49 |
| GstE9 | Glutathione S transferase E9 | 0.0461 | 1.49 |
| CG5734 | CG5734 gene product from transcript CG5734-RA | 0.0464 | 1.49 |
| MP1 | Melanisation protease 1 | 0.0000 | 1.48 |
| CG4210 | CG4210 gene product from transcript CG4210-RA | 0.0133 | 1.48 |
| Su(Ste):CR42440 | ncRNA | 0.0221 | 1.48 |
| snoRNA: Me28S-C3420a | ncRNA | 0.0284 | 1.48 |
| MalB1 | Maltase B1 | 0.0017 | 1.46 |
| CG34424 | CG34424 gene product from transcript CG34424-RA | 0.0068 | 1.46 |
| CG31743 | CG31743 gene product from transcript CG31743-RA | 0.0085 | 1.45 |
| CG34313 | CG34313 gene product from transcript CG34313-RA | 0.0085 | 1.45 |
| CG43252 | CG43252 gene product from transcript CG43252-RA | 0.0115 | 1.45 |
| CG9928 | CG9928 gene product from transcript CG9928-RA | 0.0219 | 1.45 |
| CG6045 | CG6045 gene product from transcript CG6045-RA | 0.0056 | 1.44 |
| Mlp60A | Muscle LIM protein at 60A | 0.0253 | 1.44 |
| CG34193 | CG34193 gene product from transcript CG34193-RA | 0.0388 | 1.43 |
| Bbx | Bobby sox | 0.0051 | 1.42 |
| CG42578 | CG42578 gene product from transcript CG42578-RA | 0.0424 | 1.42 |
| CG10710 | CG10710 gene product from transcript CG10710-RA | 0.0054 | 1.41 |
| CG18067 | CG18067 gene product from transcript CG18067-RA | 0.0176 | 1.41 |
| GstD9 | Glutathione S transferase D9 | 0.0382 | 1.41 |
| CG34054 | CG34054 gene product from transcript CG34054-RA | 0.0466 | 1.41 |
| CG11313 | CG11313 gene product from transcript CG11313-RC | 0.0137 | 1.40 |
| His3.3A; His3.3B | Histone H3.3A; histone H3.3B | 0.0201 | 1.40 |
| TwdlN | TweedleN | 0.0403 | 1.40 |
| Yp2 | Yolk protein 2 | 0.0446 | 1.40 |
| CG17549 | CG17549 gene product from transcript CG17549-RB | 0.0184 | 1.39 |
| CG30484 | CG30484 gene product from transcript CG30484-RB | 0.0249 | 1.39 |
| CG5612 | CG5612 gene product from transcript CG5612-RA | 0.0272 | 1.39 |
| Cyp12c1 | CG4120 gene product from transcript CG4120-RA | 0.0425 | 1.39 |
| Ppk21 | Pickpocket 21 | 0.0473 | 1.39 |
| CG32708 | CG32708 gene product from transcript CG32708-RA | 0.0166 | 1.38 |
| CG9220 | CG9220 gene product from transcript CG9220-RC | 0.0309 | 1.38 |
| GNBP3 | Gram-negative bacteria binding protein 3 | 0.0408 | 1.38 |
| snoRNA: Psi18S-1854a | ncRNA | 0.0114 | 1.37 |
| Cyp9b2 | Cytochrome P450-9b2 | 0.0163 | 1.36 |
| IM3 | Immune induced molecule 3 | 0.0204 | 1.36 |
| Calx | $Na^+/Ca^{2+}$-exchange protein | 0.0111 | 1.35 |
| Obp99a | Odourant-binding protein 99a | 0.0221 | 1.35 |

TABLE 8-continued

List of genes significantly regulated by PFJ in larval fat bodies (Experiment 4)

| Gene Symbol | Description | ANOVA P-Value | Fold Change |
|---|---|---|---|
| CG34105; CG12491 | CG34105 gene product from transcript CG34105-RA; CG12491 gene product from transcript CG12491-RA | 0.0247 | 1.35 |
| CG33679 | CG33679 gene product from transcript CG33679-RA | 0.0463 | 1.35 |
| NitFhit | Nitrilase and fragile histidine triad fusion protein | 0.0048 | 1.34 |
| CG2736 | CG2736 gene product from transcript CG2736-RA | 0.0071 | 1.34 |
| CG14053 | CG14053 gene product from transcript CG14053-RB | 0.0169 | 1.34 |
| Sod2 | Superoxide dismutase 2 (Mn) | 0.0268 | 1.34 |
| CR43644 | ncRNA | 0.0375 | 1.34 |
| CG3621 | CG3621 gene product from transcript CG3621-RA | 0.0452 | 1.34 |
| Gr36b | Gustatory receptor 36b | 0.0269 | 1.33 |
| Phk-3 | Pherokine 3 | 0.0269 | 1.33 |
| Car | Carnation | 0.0312 | 1.33 |
| CG32230 | CG32230 gene product from transcript CG32230-RC | 0.0375 | 1.33 |
| CR43628 | ncRNA | 0.0395 | 1.33 |
| CG14516 | CG14516 gene product from transcript CG14516-RB | 0.0417 | 1.33 |
| Gapdh2 | Glyceraldehyde 3 phosphate dehydrogenase 2 | 0.0425 | 1.33 |
| Nf-YB | Nuclear factor Y-box B | 0.0442 | 1.33 |
| CG13022 | CG13022 gene product from transcript CG13022-RB | 0.0057 | 1.32 |
| CG1814 | CG1814 gene product from transcript CG1814-RC | 0.0078 | 1.32 |
| CG13937 | CG13937 gene product from transcript CG13937-RI | 0.0347 | 1.32 |
| CG43890 | CG43890 gene product from transcript CG43890-RA | 0.0466 | 1.32 |
| CG11192 | CG11192 gene product from transcript CG11192-RB | 0.0483 | 1.32 |
| CG14105 | CG14105 gene product from transcript CG14105-RA | 0.0486 | 1.32 |
| mRpS34 | Mitochondrial ribosomal protein S34 | 0.0205 | 1.31 |
| CG15322 | CG15322 gene product from transcript CG15322-RB | 0.0372 | 1.31 |
| Genes Down-Regulated in Larval Fat Bodies | | | |
| CHKov2 | CG10675 gene product from transcript CG10675-RA | 0.0018 | −1.31 |
| Cap-G | CG34438 gene product from transcript CG34438-RF | 0.0046 | −1.31 |
| DppIII | Dipeptidyl aminopeptidase III | 0.0060 | −1.31 |
| CG9626 | CG9626 gene product from transcript CG9626-RC | 0.0292 | −1.31 |
| CG6179 | CG6179 gene product from transcript CG6179-RA | 0.0348 | −1.31 |
| CG15312 | CG15312 gene product from transcript CG15312-RE | 0.0118 | −1.32 |
| Sqh | Spaghetti squash | 0.0344 | −1.32 |
| CG11374 | CG11374 gene product from transcript CG11374-RC | 0.0039 | −1.33 |
| CG12942 | CG12942 gene product from transcript CG12942-RA | 0.0046 | −1.33 |
| Klp10A | CG1453 gene product from transcript CG1453-RD | 0.0068 | −1.33 |
| Nle | Notchless | 0.0120 | −1.33 |
| IFa | IFamide | 0.0050 | −1.34 |
| Usp7 | Ubiquitin-specific protease 7 | 0.0399 | −1.34 |
| CG44001; CG33995; CG44000 | CG44001 gene product from transcript CG44001-RA; CG33995 gene product from transcript CG33995-RB; CG44000 gene product from transcript CG44000-RC | 0.0420 | −1.34 |
| CG4996 | CG4996 gene product from transcript CG4996-RA | 0.0424 | −1.34 |
| TfIIB | Transcription factor IIB | 0.0078 | −1.35 |
| Dip3 | Dorsal interacting protein 3 | 0.0480 | −1.35 |
| CG13482 | CG13482 gene product from transcript CG13482-RA | 0.0029 | −1.37 |
| CG11980 | CG11980 gene product from transcript CG11980-RC | 0.0274 | −1.37 |
| Ada2a | CG43663 gene product from transcript CG43663-RC | 0.0046 | −1.38 |
| CG5508 | CG5508 gene product from transcript CG5508-RA | 0.0112 | −1.38 |
| MeiW68 | Meiotic W68 | 0.0365 | −1.38 |
| CG12713 | CG12713 gene product from transcript CG12713-RA | 0.0471 | −1.38 |
| Cad87A | Cadherin 87A | 0.0068 | −1.39 |
| CG32280 | CG32280 gene product from transcript CG32280-RB | 0.0245 | −1.40 |
| CG31663 | CG31663 gene product from transcript CG31663-RC | 0.0379 | −1.40 |
| CR40528; CR40507 | Ribosomal RNA | 0.0174 | −1.41 |
| CG14985 | CG14985 gene product from transcript CG14985-RB | 0.0428 | −1.41 |
| L(2)35Df | Lethal (2) 35Df | 0.0497 | −1.41 |
| Flo2 | Flotillin 2 | 0.0450 | −1.42 |
| CG30440 | CG30440 gene product from transcript CG30440-RA | 0.0231 | −1.43 |
| RunxA | CG34145 gene product from transcript CG34145-RB | 0.0234 | −1.43 |
| Liprin-alpha | CG11199 gene product from transcript CG11199-RC | 0.0123 | −1.44 |
| CG7810 | CG7810 gene product from transcript CG7810-RA | 0.0388 | −1.44 |
| Ag5r | Antigen 5-related | 0.0397 | −1.44 |
| Cyp6u1 | CG3567 gene product from transcript CG3567-RA | 0.0412 | −1.44 |
| Kay | Kayak | 0.0407 | −1.45 |
| Sld5 | CG14549 gene product from transcript CG14549-RA | 0.0090 | −1.46 |
| Mid | Midline | 0.0113 | −1.46 |
| CG15800 | CG15800 gene product from transcript CG15800-RA | 0.0310 | −1.47 |
| CG7656 | CG7656 gene product from transcript CG7656-RF | 0.0362 | −1.47 |
| Dar1 | Dendritic arbour reduction 1 | 0.0057 | −1.48 |
| Form3 | Formin 3 | 0.0101 | −1.48 |

TABLE 8-continued

List of genes significantly regulated by PFJ in larval fat bodies (Experiment 4)

| Gene Symbol | Description | ANOVA P-Value | Fold Change |
|---|---|---|---|
| E2f2 | E2F transcription factor 2 | 0.0210 | −1.48 |
| CG2614 | CG2614 gene product from transcript CG2614-RA | 0.0332 | −1.48 |
| CG13856 | CG13856 gene product from transcript CG13856-RA | 0.0410 | −1.49 |
| CG13097 | CG13097 gene product from transcript CG13097-RA | 0.0181 | −1.50 |
| Tsp42Ea | Tetraspanin 42Ea | 0.0125 | −1.51 |
| CG18507 | CG18507 gene product from transcript CG18507-RC | 0.0223 | −1.51 |
| Pad | Poils au dos | 0.0068 | −1.53 |
| ObstH | Obstructor H | 0.0122 | −1.53 |
| CG42262 | CG42262 gene product from transcript CG42262-RA | 0.0490 | −1.53 |
| CG32814 | CG32814 gene product from transcript CG32814-RB | 0.0452 | −1.54 |
| Bchs | Blue cheese | 0.0113 | −1.55 |
| CR40507; CR40508 | Ribosomal RNA | 0.0173 | −1.55 |
| CR40571 | Ribosomal RNA | 0.0173 | −1.55 |
| Egh | Egghead | 0.0235 | −1.55 |
| Mhcl | Myosin heavy chain-like | 0.0327 | −1.55 |
| Caf1-105 | CG12892 gene product from transcript CG12892-RA | 0.0468 | −1.56 |
| CG1443 | CG1443 gene product from transcript CG1443-RA | 0.0095 | −1.57 |
| CG33230 | CG33230 gene product from transcript CG33230-RA | 0.0414 | −1.57 |
| CG14949 | CG14949 gene product from transcript CG14949-RA | 0.0304 | −1.59 |
| Bw | Brown | 0.0037 | −1.60 |
| His2A | Histone H2A | 0.0293 | −1.61 |
| Muc12Ea | Mucin 12Ea | 0.0379 | −1.62 |
| Sog | Short gastrulation | 0.0307 | −1.63 |
| CG33985 | CG33985 gene product from transcript CG33985-RA | 0.0215 | −1.69 |
| CG13957 | CG13957 gene product from transcript CG13957-RB | 0.0268 | −1.70 |
| Ana3 | Anastral spindle 3 | 0.0458 | −1.71 |
| RSG7 | Regulator of G-protein signalling 7 | 0.0124 | −1.73 |
| Grp | Gag related protein | 0.0219 | −1.74 |
| Glut4EF | Glucose transporter 4 enhancer factor | 0.0340 | −1.78 |
| ObstI | Obstructor I | 0.0290 | −1.83 |
| CG6231 | CG6231 gene product from transcript CG6231-RC | 0.0074 | −1.85 |
| CG15890 | CG15890 gene product from transcript CG15890-RA | 0.0145 | −1.88 |
| CG9628 | CG9628 gene product from transcript CG9628-RA | 0.0245 | −1.95 |
| CG7567 | CG7567 gene product from transcript CG7567-RA | 0.0062 | −2.17 |
| CG7017 | CG7017 gene product from transcript CG7017-RB | 0.0394 | −2.31 |
| CG14945 | CG14945 gene product from transcript CG14945-RB | 0.0451 | −2.31 |
| CG5404 | CG5404 gene product from transcript CG5404-RA | 0.0480 | −2.31 |
| Slbo | Slow border cells | 0.0261 | −2.60 |
| ObstG | Obstructor G | 0.0040 | −2.65 |
| CG8492 | CG8492 gene product from transcript CG8492-RD | 0.0177 | −2.70 |
| CG43896 | CG43896 gene product from transcript CG43896-RC | 0.0006 | −3.48 |

Functional enrichment analysis on gene ontologies (biological processes) showed that genes involved in defence response and determination of adult lifespan were up-regulated, while cell cycle and growth genes were down-regulated (Table 9).

TABLE 9

List of gene ontologies (biological processes) significantly regulated by PFJ in larval fat bodies (Experiment 4)

| Ontology ID | Ontology Name | Number of Genes Changed | Percent Changed | Z Score | Permuted p Value |
|---|---|---|---|---|---|
| Gene Ontologies (Biological Processes) Up-Regulated in Larval Fat Bodies | | | | | |
| GO: 0035079 | Polytene chromosome puffing | 6 | 85.7143 | 20.8913 | 0.0000 |
| GO: 0001666 | Response to hypoxia | 6 | 13.0435 | 7.5404 | 0.0000 |
| GO: 0051707 | Response to other organism | 12 | 7.1856 | 7.3274 | 0.0000 |
| GO: 0006952 | Defence response | 12 | 6.2827 | 6.6697 | 0.0000 |
| GO: 0008152 | Metabolic process | 66 | 1.6815 | 3.8573 | 0.0005 |
| GO: 0008340 | Determination of adult lifespan | 4 | 3.4483 | 2.3129 | 0.0350 |
| Gene Ontologies (Biological Processes) Down-Regulated in Larval Fat Bodies | | | | | |
| GO: 0006333 | Chromatin assembly or disassembly | 21 | 16.8000 | 20.6634 | 0.0000 |

TABLE 9-continued

List of gene ontologies (biological processes) significantly regulated by PFJ in larval fat bodies (Experiment 4)

| Ontology ID | Ontology Name | Number of Genes Changed | Percent Changed | Z Score | Permuted p Value |
|---|---|---|---|---|---|
| GO: 0071824 | Protein-DNA complex subunit organisation | 3 | 8.5714 | 5.2991 | 0.0010 |
| GO: 0007298 | Border follicle cell migration | 4 | 5.7971 | 4.8032 | 0.0035 |
| GO: 0060560 | Developmental growth involved in morphogenesis | 3 | 5.7692 | 4.1432 | 0.0075 |
| GO: 0006030 | Chitin metabolic process | 4 | 4.3011 | 3.9222 | 0.0060 |
| GO: 0016049 | Cell growth | 3 | 4.8387 | 3.6842 | 0.0125 |
| GO: 0000278 | Mitotic cell cycle | 3 | 4.3478 | 3.4192 | 0.0110 |
| GO: 0045165 | Cell fate commitment | 3 | 2.8846 | 2.4864 | 0.0380 |
| GO: 0031399 | Regulation of protein modification process | 3 | 2.8037 | 2.4260 | 0.0380 |

For these larval fat bodies data, regulatory network analysis showed that 53 out of 161 up-regulated genes could be mapped onto human orthologues, and 13 relationships were identified between the mapped genes, with 27 unconnected entities removed (FIG. 1B).

The SOD (superoxide dismutase) or Sod2 (superoxide dismutase 2) gene appeared to be one of the nodes plotted in this regulatory network. It is also interesting to note that the fold changes for these nodes were not especially high (i.e. less than 2), while the fold changes of the heat shock proteins were mostly above 2. This might reflect the amplification cascades of signal transduction processes. On the other hand, 35 out of 84 down-regulated genes could be mapped onto human orthologues, but no relationships between these mapped genes could be identified.

It was thus the objective of this invention to conduct nutritional programming by supplementation with PFJ at the developmental stage to determine effects on adult health, using Drosophila as a model. The results indicated that this was indeed the case and has important implications on the effect on prenatal diet on the subsequent long-term health of an adult. It was also the aim of the invention to increase longevity by supplementation of adults with PFJ using the same model.

The invention claimed is:

1. A method for modulating the target of rapamycin (TOR) pathway, superoxide dismutase (Sod), superoxide dismutase 2 (Sod2), and heat shock proteins in a subject, said method comprising the steps, orally administering to said subject fractions of ethyl acetate extracted palm fruit juice obtained from palm oil mill vegetation liquor from oil palm milling, wherein said fraction is administered to said subject in an effective amount to modulate TOR pathway, Sod, Sod2, and heat shock proteins, wherein said fractions of ethyl acetate extracted palm fruit juice is obtained from said vegetation liquor using High Performance Liquid Chromatography (HPLC) separation, and wherein said fractions are selected from the group consisting of shikimic acid, p-hydroxybenzoic acid, and caffeoylshikimic acid.

2. The method for modulating TOR pathway, Sod, Sod2, and heat shock proteins in a subject of claim 1, wherein the method includes administration of fractions of ethyl acetate extracted palm fruit juice as a pharmaceutical composition, a nutraceutical composition, or a dietary supplement.

3. The method for modulating TOR pathway, Sod, Sod2, and heat shock proteins in a subject of claim 1, wherein the subject is a human.

4. The method for modulating TOR pathway, Sod, Sod2, and heat shock proteins in a subject of claim 1, wherein said administered fractions of ethyl acetate extracted palm fruit juice further comprises pharmaceutically acceptable carriers selected from the group consisting of saline, starches, sugars, gels, lipids, waxes, glycerol, solvents, oils, liquids, proteins, glycols, electrolyte solutions, alcohols, fillers, binders, emulsifiers, humectants, preservatives, buffers, colorants, emollients, foaming agents, sweeteners, thickeners, surfactants, additives and solvents and mixtures thereof.

5. The method of claim 1, wherein said modulation of TOR pathway, Sod, Sod2, and heat shock proteins in a subject delays ageing process and promotes longevity in said subject.

* * * * *